US009603948B2

(12) United States Patent
Santamaria

(10) Patent No.: US 9,603,948 B2
(45) Date of Patent: Mar. 28, 2017

(54) METHODS AND COMPOSITIONS FOR TREATING MULTIPLE SCLEROSIS AND RELATED DISORDERS

(71) Applicant: UTI Limited Partnership, Calgary (CA)

(72) Inventor: Pedro Santamaria, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 0 days.

(21) Appl. No.: 14/684,153

(22) Filed: Apr. 10, 2015

(65) Prior Publication Data

US 2015/0209446 A1      Jul. 30, 2015

Related U.S. Application Data

(63) Continuation of application No. PCT/IB2013/003033, filed on Oct. 11, 2013, which is a continuation-in-part of application No. 13/830,521, filed on Mar. 14, 2013.

(60) Provisional application No. 61/712,733, filed on Oct. 11, 2012.

(51) Int. Cl.
*A61K 47/48* (2006.01)
*A61K 39/00* (2006.01)

(52) U.S. Cl.
CPC .... *A61K 47/48861* (2013.01); *A61K 39/0008* (2013.01); *A61K 47/48015* (2013.01); *A61K 47/48215* (2013.01); *A61K 2039/55555* (2013.01); *A61K 2039/60* (2013.01); *A61K 2039/605* (2013.01); *A61K 2039/627* (2013.01); *Y10T 428/2982* (2015.01)

(58) Field of Classification Search
None
See application file for complete search history.

(56) References Cited

U.S. PATENT DOCUMENTS

| | | |
|---|---|---|
| 4,367,110 A | 1/1983 | Yoshikawa |
| 4,414,148 A | 11/1983 | Jansen et al. |
| 4,452,901 A | 6/1984 | Gordon et al. |
| 4,478,946 A | 10/1984 | Van der Merwe et al. |
| 4,554,101 A | 11/1985 | Hopp |
| 4,569,789 A | 2/1986 | Blattler et al. |
| 4,589,071 A | 5/1986 | Yamamuro et al. |
| 4,589,330 A | 5/1986 | Teron |
| 4,659,839 A | 4/1987 | Nicolotti et al. |
| 4,671,958 A | 6/1987 | Rodwell et al. |
| 4,680,338 A | 7/1987 | Sundoro |
| 4,699,784 A | 10/1987 | Shih et al. |
| 4,818,542 A | 4/1989 | DeLuca et al. |
| 5,258,499 A | 11/1993 | Konigsberg et al. |
| 5,543,391 A | 8/1996 | Yatvin et al. |
| 5,676,928 A | 10/1997 | Klaveness et al. |
| 5,840,839 A | 11/1998 | Wang et al. |
| 6,103,379 A | 8/2000 | Margel et al. |
| 6,387,498 B1 | 5/2002 | Coulter et al. |
| 6,651,655 B1 | 11/2003 | Licalsi et al. |
| 6,688,494 B2 | 2/2004 | Pozarnsky et al. |
| 6,712,997 B2 | 3/2004 | Won et al. |
| 6,797,514 B2 | 9/2004 | Berenson et al. |
| 6,846,474 B2 | 1/2005 | Nayfeh et al. |
| 6,929,675 B1 | 8/2005 | Bunge et al. |
| 7,060,121 B2 | 6/2006 | Lin et al. |
| 7,285,289 B2 | 10/2007 | Nagy et al. |
| 7,326,399 B2 | 2/2008 | Zhou et al. |
| 7,332,586 B2 | 2/2008 | Franzen et al. |
| 7,361,733 B2 | 4/2008 | Hershberg et al. |
| 7,572,631 B2 | 8/2009 | Berenson et al. |
| 8,354,110 B2 | 1/2013 | Santamaria et al. |
| 8,835,144 B2 | 9/2014 | Jiang et al. |
| 9,149,440 B2 | 10/2015 | Turos et al. |
| 2003/0068363 A1 | 4/2003 | Clark et al. |
| 2004/0137642 A1 | 7/2004 | Erfle et al. |
| 2004/0265392 A1 | 12/2004 | Tovar et al. |
| 2005/0003431 A1 | 1/2005 | Wucherpfennig et al. |
| 2005/0118102 A1 | 6/2005 | Xiang et al. |
| 2005/0129617 A1 | 6/2005 | Tan et al. |
| 2005/0202032 A1 | 9/2005 | Kaufman et al. |
| 2006/0219239 A1 | 10/2006 | Plaschkes |
| 2007/0054337 A1 | 3/2007 | Ferning et al. |
| 2007/0059775 A1 | 3/2007 | Hultman et al. |
| 2007/0129307 A1 | 6/2007 | Tan et al. |
| 2007/0154953 A1 | 7/2007 | Brunner et al. |
| 2009/0155292 A1 | 6/2009 | Santamaria et al. |
| 2009/0258355 A1 | 10/2009 | Maye et al. |
| 2010/0061984 A1 | 3/2010 | Greene et al. |

(Continued)

FOREIGN PATENT DOCUMENTS

| | | |
|---|---|---|
| CA | 2717719 A | 8/2009 |
| EP | 0 188 256 | 7/1986 |

(Continued)

OTHER PUBLICATIONS

U.S. Appl. No. 15/019,857, filed Feb. 9, 2016.
Advisory Action for U.S. Appl. No. 12/044,435, dated Aug. 23, 2011.
Aichele, P. et al. (1994) "Peptide-induced T-cell tolerance to prevent autoimmune diabetes in a transgenic mouse model," Proc. Natl. Acad. Sci. USA 91:444-448.
Amrani, A. et al. (2000) "Progression of autoimmune diabetes driven by avidity maturation of a T-cell population," Nature 406:739-742.
Amrani, A. et al. (2001) "Expansion of the Antigenic Repertoire of a Single T Cell Receptor upon T Cell Activation," J. Immunol. 167:655-666.
Anderson, B. et al. (1999) "Prevalent CD8(+) T cell response against one peptide/MHC complex in autoimmune diabetes," Proc. Natl. Acad. Sci. USA 96:9311-9316.

(Continued)

*Primary Examiner* — John Ulm
(74) *Attorney, Agent, or Firm* — Foley & Lardner LLP; Antoinette F. Konski; Lydia B. Choi

(57) ABSTRACT

This disclosure provides therapeutic compositions and methods for treating multiple sclerosis or a multiple sclerosis-related disorder in a subject in need thereof comprising administering an effective amount of an antigen-MHC-nanoparticle complex to the subject, wherein the antigen is a multiple sclerosis-related antigen.

24 Claims, 17 Drawing Sheets

(56) References Cited

U.S. PATENT DOCUMENTS

| | | |
|---|---|---|
| 2010/0104503 A1 | 4/2010 | Mellman et al. |
| 2010/0303866 A1 | 12/2010 | Saint-Remy |
| 2011/0059121 A1 | 3/2011 | Santamaria et al. |
| 2011/0250146 A1 | 10/2011 | Zhang et al. |
| 2012/0093934 A1 | 4/2012 | Santamaria |
| 2012/0121649 A1 | 5/2012 | Santamaria |
| 2013/0128138 A1 | 5/2013 | Kuo et al. |
| 2013/0302421 A1 | 11/2013 | Santamaria et al. |
| 2013/0330414 A1 | 12/2013 | Santamaria |
| 2014/0105980 A1 | 4/2014 | Santamaria |
| 2014/0341938 A1 | 11/2014 | Rademacher et al. |
| 2014/0370099 A1 | 12/2014 | Green et al. |
| 2015/0125536 A1 | 5/2015 | Santamaria |
| 2015/0150996 A1 | 6/2015 | Miller et al. |
| 2015/0250871 A1 | 9/2015 | Santamaria |

FOREIGN PATENT DOCUMENTS

| | | |
|---|---|---|
| JP | 2001-516571 A | 10/2001 |
| WO | WO-92/18150 A1 | 10/1992 |
| WO | WO-93/16725 A1 | 9/1993 |
| WO | WO-99/14236 A1 | 3/1999 |
| WO | WO-2004/078909 A2 | 9/2004 |
| WO | WO-2005/033267 A2 | 4/2005 |
| WO | WO-2006/080951 A2 | 8/2006 |
| WO | WO-2007/024026 | 3/2007 |
| WO | WO-2008/109852 A2 | 9/2008 |
| WO | WO-2008/118861 A2 | 10/2008 |
| WO | WO-2009/040811 A2 | 4/2009 |
| WO | WO-2009/078799 | 6/2009 |
| WO | WO-2009/094273 A2 | 7/2009 |
| WO | WO-2009/111588 A1 | 9/2009 |
| WO | WO-2010/080032 A2 | 7/2010 |
| WO | WO-2010/085509 A1 | 7/2010 |
| WO | WO-2011/073685 A1 | 6/2011 |
| WO | WO-2011/104497 A1 | 9/2011 |
| WO | WO 2012/031258 A1 | 3/2012 |
| WO | WO-2012/041968 A1 | 4/2012 |
| WO | WO 2013/043662 A1 | 3/2013 |
| WO | WO-2013/144811 A2 | 10/2013 |

OTHER PUBLICATIONS

Anderton, S.M. et al. (1998) "Hierarchy in the ability of T cell epitopes to induce peripheral tolerance to antigens from myelin," Eur. J. Immunol. 28:1251-1261.

Appay, V. et al. (2000) "HIV-specific CD8(+) T Cells Produce Antiviral Cytokines but Are Impaired in Cytoltic Function," J. Exp. Med. 192(1):63-72.

Author Unknown (2002) Diabetes Prevention Trial-Type 1 Diabetes Study Group, "Effects of Insulin in Relatives of Patients with Type 1 Diabetes Mellitus," N. Engl. J. Med. 346:1685-1691.

Author Unknown (2010) KidsHealth from Nemours, "Can Diabetes Be Prevented?," Website article from kidshealth.org/PageManager. jsp?dn=KidsHealth&lic=1&ps=107&caUd=139 downloaded Nov. 9, 2010, 2 pages.

Bachmann, M.F. et al. (1999) "Developmental Regulation of Lck Targeting to the CD8 Coreceptor Controls Signaling in Naive and Memory T Cells," J. Exp. Med. 189:1521-1530.

Barber, D.L. et al. (2006) "Restoring function in exhausted CD8 T cells during chronic viral infection," Nature 439:682-687.

Becker, T.C. et al. (2002) "Interleukin 15 Is Required for Proliferative Renewal of Virus-specific Memory CD8 T Cells," J. Exp. Med. 195(12):1541-1548.

Behan, P.O. et al. (2010) "The sad plight of multiple sclerosis research (low on fact, high on fiction): critical data to support it being a neurocristopathy," Inflammopharmacol 18:265-290.

Betts, R.J. et al. (2009) "CD8( ) T cells in asthma: Friend or foe?" Pharmacology & Therapeutics 121:123-131.

Bibliographic data page from Epo website at espacenet. com/publicationDetails/biblio?CC=WO&NR=2004078909A2 &KC= . . ., downloaded Nov. 15, 2010, showing that WO2004078909 was also published as US2007154953: 1 page total.

Bielekova, B. et al. (2000) "Encephalitogenic potential of the myelin basic protein peptide (amino acids 83-99) in multiple sclerosis: Results of a phase II clinical trial with an altered peptide ligand," Nat. Med. 6(10):1167-1175.

Blancou, P. et al. (2007) "Immunization of HLA Class I Transgenic Mice Identifies Autoantigenic Epitopes Eliciting Dominant Responses in Type 1 Diabetes Patients," J. Immunol. 178:7458-7466.

Bottazzo, G.F. et al. (1985) "In situ characterization of autoimmune phenomena and expression of HLA molecules in the pancreas in diabetic insulitis," N. Engl. J. Med. 313(6):353-360.

Bottini, M. et al. (2007) "Luminescent Silica Nanobeads: Characterization and Evaluation as Efficient Cytoplasmatic Transporters for T-Lymphocytes," J. Am. Chem. Soc. 129(25):7814-7823.

Bour-Jordan, H. et al. (2007) "B cell depletion: a novel therapy for autoimmune diabetes?" J. Clin. Invest. 117:3642-3645.

Braud, V.M. et al. (1999) "Functions of nonclassical MHC and non-MHC-encoded class I molecules," Current Opinion in Immunology 11:100-108.

Cao, K. et al. (2001) "Analysis of the Frequencies of HLA-A, B, and C Alleles and Haplotypes in the Five Major Ethnic Groups of the United States Reveals High Levels of Diversity in These Loci and Contrasting Distribution Patterns in These Populations," Hum. Immunol. 62:1009-1030.

Chang, J.W. et al. (2001) "Design, engineering, and production of human recombinant T-cell receptor ligands derived from human leukocyte antigen DR2," Journal of Biological Chemistry 276(26):24170-6.

Chatenoud, L. (2002) "Do NKT cells control autoimmunity?" J. Clin. Invest. 110(6):747-748.

Cirillo, C. et al. (2011) "S100B protein in the gut: The evidence for enteroglial-sustained intestinal inflammation," World J Gastroenterol. 17(10):1261-1266.

Constantinescu, C.S. et al. (2011) "Experimental autoimmune encephalomyelitis (EAE) as a model for multiple sclerosis (MS)," British Journal of Pharmacology 164:1079-1106.

Croxford, A.L. et al. (2011) "Mouse models for multiple sclerosis: Historical facts and future implications," Biochimica et Biophysica Acta 1812:177-183.

Cuiv, P.O. et al. (2011) "Draft Genome Sequence of Bacteroides vulgatus PC510, a Strain Isolated from Human Feces," Journal of Bacteriology 193(15):4025-4026.

Database Accession No. ADK001000110 (2011) "Bacteroides vulgatus PC510 contig00041, whole genome shotgun sequence.".

Database Accession No. D4VD94 (2010) "Subname: Full=Conserved domain protein," from www.uniprot.org/uniprot/D4VD94.

Denic, A. et al. (2011) "The relevance of animal models in multiple sclerosis research," Pathophysiology 18:21-29.

DiLorenzo, T.P. et al. (1998) "Major histocompatibility complex class I-restricted T cells are required for all but the end stages of diabetes development in nonobese diabetic mice and use a prevalent T cell receptor alpha chain gene rearrangement," Proc. Natl. Acad. Sci. USA 95:1253812543.

Dominguez, A.L. et al. (2010) "Targeting the tumor microenvironment with anti-neu/anti-CD40 conjugated nanoparticles for the induction of antitumor immune responses," Vaccine 28(5):1383-1390.

Dressel, A. et al. (1997) "Autoantigen recognition by human CD8 T cell clones: enhanced agonist response induced by altered peptide ligands," J. Immunol. 159: 4943-4951.

Eggena, M. et al. (2000) "Identification of Histone H1 as a Cognate Antigen of the Ulcerative Colitis-associated Marker Antibody pANCA," Journal of Autoimmunity 14:83-97.

Fennessy, M. et al. (1994) "A gene in the HLA class I region contributes to susceptibility to IDDM in the Finnish population," Diabetologia 37:937-944.

Final Office Action for U.S. Appl. No. 12/044,435, dated Jun. 8, 2011.

Final Office Action for U.S. Appl. No. 12/848,055, dated Aug. 23, 2012.

(56) References Cited

OTHER PUBLICATIONS

Final Office Action for U.S. Appl. No. 12/848,055, dated Dec. 24, 2014.
Final Office Action for U.S. Appl. No. 12/848,055, dated Jul. 12, 2013.
Final Office Action for U.S. Appl. No. 13/249,105, dated Nov. 30, 2015.
Final Office Action for U.S. Appl. No. 13/830,521, dated Mar. 5, 2015.
Final Office Action for U.S. Appl. No. 13/842,302, dated Feb. 18, 2015.
Final Office Action for U.S. Appl. No. 14/723,268, dated Mar. 30, 2016.
Flad, T. et al. (2003) "Development of an MHC-class I peptide selection assay combining nanoparticle technology and matrix-assisted laser desorption/ionisation mass spectrometry," J. Immunol. Meth. 283:205-213.
Gill, R.G. et al. (1989) "Characterization of Primary T Cell Subsets Mediating Rejection of Pancreatic Islet Grafts," Journal of Immunology 143(7):2176-2178.
Gimmi, C.D. et al. (1993) "Human T-cell clonal anergy is induced by antigen presentation in the absence of B7 costimulation," Proc. Natl. Acad. Sci. USA 90:6586-6590.
Gold, R. et al. (2006) "Understanding pathogenesis and therapy of multiple sclerosis via animal models: 70 years of merits and culprits in experimental autoimmune encephalomyelitis research," Brain 129:1953-1971.
Gregori, S. et al. (2008) "Re-establishing immune tolerance in type 1 diabetes via regulatory T cells," Novartis Found Symp. 292:abstract.
Guarda, G. et al. (2007) "L-selectin-negative CCR7(-) effector and memory CD8(+) T cells enter reactive lymph nodes and kill dendritic cells," Nat. Immunol. 8(7):743-752.
Gupta, A.K. et al. (2005) "Synthesis and surface engineering of iron oxide nanoparticles for biomedical applications," Biomaterials 26:3995-4021.
Hamilton-Williams, E.E. et al. (2001) "Transgenic rescue implicates beta2-microglobulin as a diabetes susceptibility gene in nonobese diabetic (NOD) mice," Proc. Natl. Acad. Sci. USA 98(20): 11533-11538.
Han, B. et al. (2005) "Developmental control of CD8(+) T cell-avidity maturation in autoimmune diabetes," J. Clin. Invest. 115(7):1879-1887.
Han, B. et al. (2005) "Prevention of diabetes by manipulation of anti-IGRP autoimmunity: high efficiency of a low-affinity peptide," Nat. Med. 11:645-652.
Han, G. et al. (2009) "Interleukin-17-producing ys T Cells protect Nod mice from type 1 diabetes through a mechanism involving transforming growth factor-b," Immunology 129:197-206.
Hassainya, Y. et al. (2005) "Identification of Naturally Processed HLA-A2—Restricted Proinsulin Epitopes by Reverse Immunology," Diabetes 54:2053-2059.
Herold, K.C. et al. (2002) "Anti-CD3 monoclonal antibody in new onset type I diabetes mellitus," N. Eng. J. Med. 346:1692-1698.
Holgate, S.T. et al. (2008) "Treatment strategies for allergy and asthma," Nature 8:218-230.
Honeyman, M.C. et al. (1995) "Analysis of Families at Risk for Insulin-Dependent Diabetes Mellitus Reveals that HLA Antigens Influence Progression to Clinical Disease," Molecular Medicine 1(5):576582.
International Search Report and Written Opinion (ISA/CA) for International Application No. PCT/IB2014/003014, dated May 12, 2015, 15 pages.
International Search Report and Written Opinion (ISA/EP) for International Application No. PCT/EP2011/066994, mailed Nov. 21, 2011, 10 pages.
International Search Report and Written Opinion (ISA/EP) for International Application No. PCT/IB2013/052352, dated Oct. 2, 2013, 4 pages.
Itoh, N. et al. (1993) "Mononuclear Cell Infiltration and Its Relation to the Expression of Major Histocompatibility Complex Antigens and Adhesion Molecules in Pancreas Biopsy Specimens from Newly Diagnosed Insulin-dependent Diabetes Mellitus Patients," J. Clin. Invest. 92:2313-2322.
Japan Intractable Diseases Information Center (2015) "Crohn's Disease," http://www.nanbyou.or.jp/entry/111.
Japan Intractable Diseases Information Center (2015) "Sjogren's Syndrome," http://www.nanbyou.or.jp/entry/81.
Jarchum, I. et al. (2007) "In Vivo Cytotoxicity of Insulin-Specific CD8(+) T-Cells in HLA-A*0201 Transgenic NOD Mice," Diabetes 56:2551-2560.
Jarchum, I. et al. (2008) "Identification of novel IGRP epitopes targeted in type 1 diabetes patients," Clin. Immunol. 127:359-365.
Judge, A.D. et al. (2002) "Interleukin 15 Controls both Proliferation and Survival of a Subset of Memory-Phenotype CD8(+) T Cells," J. Exp. Med. 196(7):935-946.
Jun, H-S. et al. (2003) "A new look at viruses in type 1 diabetes," Diabetes Metab. Res. Rev. 19:831.
Jurewicz, A. et al. (1998) "MHc Class I-Restricted Lysis of Human Oligodendrocytes by Myelin Basic Protein Peptide-Specific CD8 T Lymphocytes," J. Immunol. 160:3056-3059.
Kappos, L. et al. (2000) "Induction of a non-encephalitogenic type 2 T helper-cell autoimmune response in multiple sclerosis after administration of an altered peptide ligand in a placebo-controlled, randomized phase II trial," Nat. Med. 6(10):1176-1182.
Karin, N. et al. (1994) "Reversal of Experimental Autoimmune Encephalomyelitis by a Soluble Peptide Variant of a Myelin Basic Protein Epitope: T Cell Receptor Antagonism and Reduction of Interferon gamma and Tumor Necrosis Factor alpha Production," J. Exp. Med. 180:2227-2237.
Karounos, D.G. et al. (1997) "Metabolically Inactive Insulin Analog Prevents Type I Diabetes in Prediabetic NOD Mice," J. Clin. Invest. 100:1344-1348.
Kent, S.C. et al. (2005) "Expanded T cells from pancreatic lymph nodes of type 1 diabetic subjects recognize an insulin epitope," Nature 435:224-228.
Keymeulen, B. et al. (2005) "Insulin Needs after CD3-Antibody Therapy in New-Onset Type 1 Diabetes," N. Engl. J. Med. 352:2598-2608.
Kim, S-K. et al. (1999) "Induction and Visualization of Mucosal Memory CD8 T Cells Following Systemic Virus Infection," J. Immunol. 163:4125-4132.
Komai-Koma, M. et al. (2004) "TLR2 is expressed on activated T cells as a costimulatory receptor," PNAS 101(9):3029-3034.
Krishnamoorthy, G. et al. (2009) "Myelin-specific T cells also recognize neuronal autoantigen in a transgenic mouse model of multiple sclerosis," Nature Medicine 15(6):626-633.
Kukreja, A. et al. (2002) "NKT Cells and Type-1 Diabetes and the "hygiene Hypothesis" to Explain the Rising Incidence Rate," Diabetes Technology & Therapeutics 4(3):323-333.
Kulmala, P. (2003) "Prediabetes in Children," Pediatr Drugs, 5(4):211-221.
Kwong, B. et al. (2010) "Synthesis and characterization of antibody-nanoparticle conjugates for locally sequestered tumor immunotherapy," Abstracts of Papers American Chemical Society 240(POLY 61):POLY.
Lechner, F. et al. (2000) "Analysis of Successful Immune Responses in Persons Infected with Hepatitis C Virus," J. Exp. Med. 191(9):1499-1512.
Lee, Y. et al. (2010) "Biodegradable Nanoparticles Containing TLR3 or TLR9 Agonists Together with Antigen Enhance MHC-restricted Presentation of the Antigen," Arch. Pharm. Res. 33(11):1859-1866.
Liblau, R.S. et al. (2002) "Autoreactive CD8 T cells in Organ-Specific Autoimmunity: Emerging Targets for Therapeutic Intervention," Immunity 17:1-6.
Lieberman, S.M. et al. (2003) "A comprehensive guide to antibody and T-cell responses in type 1 diabetes," Tissue Antigens 62:359-377.
Lieberman, S.M. et al. (2003) "Identification of the beta cell antigen targeted by a prevalent population of pathogenic CD8(+) T cells in autoimmune diabetes," PNAS 100(14):8384-8388.

(56) References Cited

OTHER PUBLICATIONS

Lieberman, S.M. et al. (2004) "Individual Nonobese Diabetic Mice Exhibit Unique Patterns of CD8(+) T Cell Reactivity to Three Islet Antigens, Including the Newly Identified Widely Expressed Dystrophia Myotonica Kinase," J. Immunol. 173:6727-6734.
Mallone, R. et al. (2007) "CD8(+) T-Cell Responses Identify beta-Cell Autoimmunity in Human Type 1 Diabetes," Diabetes 56:613-621.
Maree, A.F.M. et al. (2006) "Modeling competition among autoreactive CD8(+) T cells in autoimmune diabetes: implications for antigen-specific therapy," International Immunology 18(7):1067-1077.
Mars, L.T. et al. (2007) "CD8 T Cell Responses to Myelin Oligodendrocyte Glycoprotein-Derived Peptides in Humanized HLA-A*0201-Transgenic Mice," J. Immunol. 179:5090-5098.
McKown, K.M. et al. (1999) "Lack of efficacy of oral bovine type II collagen added to existing therapy in rheumatoid arthritis," Arthritis & Rheumatism 42(6):1204-1208.
Mescher, M.F. et al. (2006) "Signals required for programming effector and memory development by CD8(+) T cells," Immunol. Rev. 211:81-92.
Metzler, B. et al. (1993) "Inhibition of experimental autoimmune encephalomyelitis by inhalation but not oral administration of the encephalitogenic peptide: influence of MHC binding affinity," Int. Immunol. 5(9):1159-1165.
Miller, S.D. et al. (1979) "The induction of cell-mediated immunity and tolerance with protein antigens coupled to syngeneic lymphoid cells," J. Exp. Med. 149:758-773.
Moore, A. et al. (2004) "Tracking the Recruitment of Diabetogenic CD8(+) T-Cells to the Pancreas in Real Time," Diabetes 53(6):1459-1466.
Nakayama, M. et al. (2005) "Prime role for an insulin epitope in the development of type 1 diabetes in NOD mice," Nature 435(7039):220-223.
Nelson, J. et al. (2015) "6 types of asthma and how they're treated," Mother Nature Network, mnn.com.
Non-Final Office Action for U.S. Appl. No. 12/044,435, dated May 2, 2012.
Non-Final Office Action for U.S. Appl. No. 12/044,435, dated Nov. 24, 2010.
Non-Final Office Action for U.S. Appl. No. 12/848,055, dated Apr. 4, 2012.
Non-Final Office Action for U.S. Appl. No. 12/848,055, dated Dec. 19, 2012.
Non-Final Office Action for U.S. Appl. No. 12/848,055, dated Jun. 6, 2014.
Non-Final Office Action for U.S. Appl. No. 13/249,105, dated Apr. 3, 2015.
Non-Final Office Action for U.S. Appl. No. 13/712,832, dated Feb. 27, 2015.
Non-Final Office Action for U.S. Appl. No. 13/830,521, dated Jul. 25, 2014.
Non-Final Office Action for U.S. Appl. No. 13/842,302, dated Apr. 30, 2014.
Non-Final Office Action for U.S. Appl. No. 14/723,268, dated Oct. 16, 2015.
Notice of Allowance for U.S. Appl. No. 12/044,435, dated Sep. 12, 2012.
Notice to the Applicant Regarding a Non-Compliant or Non-Responsive Amendment for U.S. Appl. No. 12/044,435, dated Aug. 16, 2010.
Oh, S. et al. (2004) "IL-15 / IL-15R alpha-mediated avidity maturation of memory CD8(+) T cells," PNAS 101(42):15154-15159.
Oleszak, E.L. et al. (2004) "Theiler's Virus Infection: a Model for Multiple Sclerosis," Clinical Microbiology Reviews 17(1):174-207.
Ouyang, Q. et al. (2006) "Recognition of HLA Class I-Restricted beta-Cell Epitopes in Type 1 Diabetes," Diabetes 55:3068-3074.
Pachner, A.R. (2011) "Experimental models of multiple sclerosis," Current Opinion in Neurology 24:291-299.
Palmer, J.P. et al. (1983) "Insulin Antibodies in Insulin-Dependent Diabetics Before Insulin Treatment," Science 222:1337-1339.
Pascolo, S. et al. (1997) "HLA-A2.1-restricted Education and Cytolytic activity of CD8(+) T Lymphocytes from beta2 Microglobulin (beta2m) HLA-A2.1 Monochain Transgenic H-2D(b) beta2m Double Knockout Mice," J. Exp. Med. 185(12):2043-2051.
Petros, R. et al. (2007) "Antibody conjugation to Print nanoparticles as a cellular targeting strategy," Abstracts of Papers American Chemical Society 233(COLL 14):COLL14.
Pinkse, G.G.M. et al. (2005) "Autoreactive CD8 T cells associated with beta cell destruction in type 1 diabetes," PNAS 102(51):18425-18430.
Ransohoff, R.M. et al. (2012) "Animal models of multiple sclerosis: the good, the bad and the bottom line," Nature Neuroscience 15(8):1074-1077.
Restriction Requirement for U.S. Appl. No. 12/044,435, dated May 12, 2010.
Restriction Requirement for U.S. Appl. No. 12/848,055, dated Jan. 10, 2012.
Restriction Requirement for U.S. Appl. No. 12/848,055, dated Sep. 13, 2011.
Restriction Requirement for U.S. Appl. No. 13/249,105, dated Nov. 24, 2014.
Restriction Requirement for U.S. Appl. No. 13/712,832, dated Aug. 11, 2014.
Restriction Requirement for U.S. Appl. No. 13/830,521, dated Mar. 31, 2014.
Restriction Requirement for U.S. Appl. No. 13/842,302, dated Dec. 12, 2013.
Santamaria, P. (2001) "Effector lymphocytes in autoimmunity," Curr. Opin. Immunol. 13:663-669.
Santamaria, P. et al. (1992) "Characterization of T lymphocytes infiltrating human pancreas allograft affected by isletitis and recurrent diabetes," Diabetes 41:53-61.
Santamaria, P. et al. (1994) "Skewed T-cell receptor usage and junctional heterogeneity among isletitis alpha beta and gamma omega T cells in human Iddm (insulin-dependent diabetes mellitus)," Diabetes 43:599-606.
Santamaria, P. et al. (1995) "Beta-Cell-Cytotoxic CD8(+) T Cells from Nonobese Diabetic Mice Use Highly Homologous T Cell Receptor alpha-Chain CDR3 Sequences," J. Immunol. 154:2494-2503.
Saragovi, H.U. et al. (1999) "Small molecule and protein-based neurotrophic ligands: agonists and antagonists as therapeutic agents," Exp. Opin. Ther. Patents 9(6):737-751.
Schirle, M. et al. (2001) "Combining computer algorithms with experimental approaches permits the rapid and accurate identification of T cell epitopes from defined antigens," J. Immunol. Methods 257:1-16.
Schnutgen, F. et al. (2003) "A directional strategy for monitoring Cre-mediated recombination and the cellular level in the mouse," Nat. Biotech. 21:562-566.
Schreiber, H.A. et al. (2010) "Using carbon magnetic nanoparticles to target, track, and manipulate dendritic cells," Journal of Immunological Methods 356(1-2):47-59.
Serreze, D.V. et al. (2001) "Autoreactive Diabetogenic T-Cells in NOD Mice Can Efficiently Expand From a Greatly Reduced Precursor Pool," Diabetes 50:1992-2000.
Sibley, R.K et al. (1985) "Recurrent Diabetes Mellitus in the Pancreas Iso- and Allograf: A Light and Electron Microscopic and Immunohistochemical Analysis of Four Cases," Lab. Invest. 53(2):132-144.
Somoza, N. et al. (1994) "Pancreas in Recent Onset Insulin-Dependent Diabetes Mellitus. Changes in HLA, Adhesion Molecules and Autoantigens, Restricted T Cell Receptor V beta Usage, and Cytokine Profile," J. Immunol. 153:1360-1377.
Spada, F.M., et al. (2000) "Self-Recognition of CD1 by γ/s T Cells: Implications for Innate Immunity," J. Exp. Med. 191(6):937-948.
Sprent, J. et al. (2001) "T Cell Death and Memory," Science 293:245-248.
Sprent, J. et al. (2002) "T Cell Memory," Annu. Rev. Immunol. 20:551-579.

(56) References Cited

OTHER PUBLICATIONS

Standifer, N. E. et al. (2006) "Identification of Novel HLA-A*0201-Restricted Epitopes in Recent-Onset Type 1 Diabetic Subjects and Antibody-Positive Relatives," Diabetes 55:3061-3067.
Supplemental Notice of Allowability for U.S. Appl. No. 12/044,435, dated Dec. 13, 2012.
'T Hart, B.A. et al. (2004) "Modelling of multiple sclerosis: lessons learned in a non-human primate," Lancet Neurology 3:588-597.
Tait, B.D. et al. (1995) "HLA Antigens and Age at Diagnosis of Insulin-Dependent Diabetes Mellitus," Hum. Immunol. 42:116-124.
Takaki, T. et al. (2006) "HLA-A*0201-Restricted T Cells from Humanized NOD Mice Recognize Autoantigens of Potential Clinical Relevance to Type 1 Diabetes," J. Immunol. 176:3257-3265.
Tan, J.T. et al. (2002) "Interleukin (IL)-15 and IL-7 Jointly Regulate Homeostatic Proliferation of Memory Phenotype CD8(+) Cells but Are Not Required for Memory Phenotype CD4(+) Cells," J. Exp. Med. 195(12):1523-1532.
Toes, R.E.M. et al. (1996) "Peptide vaccination can lead to enhanced tumor growth through specific T-cell tolerance induction," Proc. Natl. Acad. Sci. USA 93:7855-7860.
Toma, A. et al. (2005) "Recognition of a subregion of human proinsulin by class I-restricted T cells in type 1 diabetic patients," Proc. Natl. Acad. Sci. USA 102(30):10581-10586.
Trenttham, D.E. et al. (1993) "Effects of Oral Administration of Type II Collagen on Rheumatoid Arthritis," Science 261:1727-1730.
Trudeau, J.D. et al. (2003) "Prediction of spontaneous autoimmune diabetes in NOD mice by quantification of autoreactive T cells in peripheral blood," J. Clin. Invest. 111:217-223.
Tsai, S. et al. (2010) "Reversal of Autoimmunity by Boosting Memory-like Autoregulatory T Cells," Immunity 32(4):568-580.
Tsuchida, T. et al. (1994) "Autoreactive CD8(+) T-cell responses to human myelin protein-derived peptides," Proc. Natl. Acad. Sci. USA, 91:10859-10863.
Unger, W.W.J. et al. (2007) "Human Clonal CD8 Autoreactivity to an IGRP Islet Epitope Shared between Mice and Men," Ann. N. Y. Acad. Sci. 1103:192-195.
UniProtKB: D4VD94 (2010) from www.uniprot.org/uniprot/D4VD94.
Van Belle, T.L. et al. (2011) "Type 1 Diabetes: Etiology, Immunology, and Therapeutic Strategies," Physiol. Rev. 91:79-118.
Vandenbark, A.A. et al. (2003) "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," Journal of Immunology 171(1):127-33.
Verdaguer, J. et al. (1996) "Acceleration of Spontaneous Diabetes in TCR-beta-Transgenic Nonobese Diabetic Mice by beta-Cell Cytotoxic CD8(+) T Cells Expressing Identical Endogenous TCR-alpha Changes," The Journal of Immunology 157:4726-4735.
Verdaguer, J. et al. (1997) "Spontaneous Autoimmune Diabetes in Monoclonal T Cell Nonobese Diabetic Mice," J. Exp. Med. 186(10):1663-1676.
Verdu, E.F. et al. (2000) "Oral administration of antigens from intestinal flora anaerobic bacteria reduces the severity of experimental acute colitis in BALB/c mice," Clin Exp Immunol. 120:46-50.
Vincent, M.S. et al. (2003) "Understanding the function of CD1-restricted T cells," Nat. Immunol. 4(6):517-523.
Wainwright, S.D. et al. (2000) "HLA-F Is a Predominantly Empty, Intracellular, TAP-Associated MHC Class lb Protein with a Restricted Expression Pattern," J. Immunol. 164(1):319-328.
Walter, U. et al. (2005) "CD8(+) T cells in autoimmunity," Curr. Opin. Immunol. 17:624-631.
Wang, X. et al. (2007) "Induction of Potent CD8(+) T-Cell Responses by Novel Biodegradable Nanoparticles Carrying Human Immunodeficiency Virus Type 1 gp120," Journal of Virology 81(18):10009-10016.
Warnock, G.L. et al. (1991) "Normoglycaemia after transplantation of freshly isolated and cryopreserved pancreatic islets in Type 1 (insulin-dependent) diabetes mellitus," Diabetologia 34:55-58.
Weiner, H.L. et al. (1993) "Double-Blind Pilot Trial of Oral Tolerization with Myelin Antigens in Multiple Sclerosis," Science 259:1321-1324.
Weiss, G.A. et al. (1996) "Covalent HLA-B27/peptide complex induced by specific recognition of an aziridine mimic of arginine," Proc. Natl. Acad. Sci. USA 93:10945-10948.
Wekerle, H. et al. (2006) "Animal models of multiple sclerosis," Drug Discovery Today: Disease Models 3(4):359-367.
Williams, M.A. et al. (2006) "Developing and maintaining protective CD8(+) memory T cells," Immunol. Rev. 211:146-153.
Winer, S. et al. (2003) "Autoimmune islet destruction in spontaneous type 1 diabetes is not beta-cell exclusive," Nat. Med. 9(2):198-205.
Wong, F.S. et al. (1999) "Identification of an MHC class I-restricted autoantigen in type 1 diabetes by screening an organ-specific cDNA library," Nat. Med. 5(9):1026-1031.
Wraith, D.C. et al. (1989) "Antigen Recognition in Autoimmune Encephalomyelitis and the Potential for Peptide-Mediated Immunotherapy," Cell 59:247-255.
Wu, W. et al. (2008) "Magnetic Iron Oxide Nanoparticles: Synthesis and Surface Functionalization Strategies," Nanoscale Res Lett. 3:397-415.
Yadav, V. et al. (2012) "Recombinant T-Cell Receptor Ligand (RTL) for Treatment of Multiple Sclerosis: A Double-Blind, Placebo-Controlled, Phase 1, Dose-Escalation Study," Autoimmune Diseases 2012(954739):1-11.
Yamanouchi, J. et al. (2007) "Interleukin-2 gene variation impairs regulatory T cell function and causes autoimmunity," Nat. Genet. 39(3):329-337.
Zajac, A.J. et al. (1998) "Viral Immune Evasion Due to Persistence of Activated T Cells Without Effector Function," J. Exp. Med. 188(12):2205-2213.
Zhang, S. et al. (2010) "HMGB1, an innate alarmin, in the pathogenesis of type 1 diabetes," Int. J. Clin. Exp. Pathol. 3(1):24-38.
International Search Report and Written Opinion (ISA/CA) for International Application No. PCT/IB2013/003033, mailed Jul. 14, 2014, 10 pages.
U.S. Appl. No. 15/348,959, filed Nov. 10, 2016, Unlimited Partnership.
Cnop, M. et al. (2005) "Mechanisms of Pancreatic beta-Cell Death in Type 1 and Type 2 Diabetes," Diabetes 54(2):597-5107.
Gunn, J. et al. (2008) "A multimodal targeting nanoparticle for selectively labeling T cells," Small. 4(6):712-715.
Mallone, R. et al. (2011) "T Cell Recognition of Autoantigens in Human Type 1 Diabetes: Clinical Perspectives," Clinical and Developmental Immunology 2011(513210):1-16.
Mei, X. et al., Chemical Industry Press (2004) Biotechnology pharmaceutic preparation: foundation and application:199.
Non-Final Office Action in U.S. Appl. No. 12/848,055, mailed May 13, 2016.
Non-Final Office Action in U.S. Appl. No. 13/830,521, mailed Jun. 28, 2016.
Non-Final Office Action in U.S. Appl. No. 13/842,302, dated Jul. 6, 2016.
Wen, Z., Nanjing University Press (2007) "3. Surface effect of the nanoparticles," Introduction to Nature Science:373-374.
Xu, H., Tsinghua University Press (2004) "13.3.3 Relationship between gene transduction and nanoparticle size," Nano Medicine:358.

```
                KpnI
              ~~~~~~~
                  NcoI
                ~~~~~~
                    M   A   I   I   Y   L   I   L   L   F   T   A   V   R   G   G
     841      GG TACCATGGCT ATCATCTACC TCATCCTCCT GTTCACCGCT GTGCGGGGCG
              CC ATGGTACCGA TAGTAGATGG AGTAGGAGGA CAAGTGGCGA CACGCCCCGC
                              NcoI                     SpeI
                            ~~~~~~                   ~~~~~~~
                 W   Y   R   S   P   F   S   R   V   V   H   G   G   G   S   L   V   P   R
     901      GCTGGTATAG AAGTCCATTT AGCCGTGTTG TCCATGGAGG TGGAGGCTCA CTAGTGCCCC
              CGACCATATC TTCAGGTAAA TCGGCACAAC AGGTACCTCC ACCTCCGAGT GATCACGGGG

G   S   G   G   G   S   G   D   S   E   R   H   F   V   Y   Q   F   M   G
     961      GAGGCTCTGG AGGTGGAGGC TCTGGAGACT CCGAAAGGCA TTTCGTGTAC CAGTTCATGG
              CTCCGAGACC TCCACCTCCG AGACCTCTGA GGCTTTCCGT AAAGCACATG GTCAAGTACC

E   C   Y   F   T   N   G   T   Q   R   I   R   Y   V   T   R   Y   I   Y   N
    1021      GCGAGTGCTA CTTCACCAAC GGGACGCAGC GCATACGATA TGTGACCAGA TACATCTACA
              CGCTCACGAT GAAGTGGTTG CCCTGCGTCG CGTATGCTAT ACACTGGTCT ATGTAGATGT

R   E   E   Y   V   R   Y   D   S   D   V   G   E   H   R   A   V   T   E   L
    1081      ACCGGGAGGA GTACGTGCGC TACGACAGCG ACGTGGGCGA GCACCGCGCG GTGACCGAGC
              TGGCCCTCCT CATGCACGCG ATGCTGTCGC TGCACCCGCT CGTGGCGCGC CACTGGCTCG

G   R   P   D   A   E   Y   W   N   S   Q   P   E   I   L   E   R   T   R   A
    1141      TGGGGCGGCC AGACGCCGAG TACTGGAACA GCCAGCCGGA GATCCTGGAG CGAACGCGGG
              ACCCCGCCGG TCTGCGGCTC ATGACCTTGT CGGTCGGCCT CTAGGACCTC GCTTGCGCCC

E   L   D   T   V   C   R   H   N   Y   E   G   P   E   T   H   T   S   L   R
    1201      CCGAGCTGGA CACGGTGTGC AGACACAACT ACGAGGGGCC GGAGACCCAC ACCTCCCTGC
              GGCTCGACCT GTGCCACACG TCTGTGTTGA TGCTCCCCGG CCTCTGGGTG TGGAGGGACG

R   L   E   Q   P   N   V   V   I   S   L   S   R   T   E   A   L   N   H   H
    1261      GGCGGCTTGA ACAGCCCAAT GTCGTCATCT CCCTGTCCAG GACAGAGGCC CTCAACCACC
              CCGCCGAACT TGTCGGGTTA CAGCAGTAGA GGGACAGGTC CTGTCTCCGG GAGTTGGTGG

N   T   L   V   C   S   V   T   D   F   Y   P   A   K   I   K   V   R   W   F
    1321      ACAACACTCT GGTCTGCTCA GTGACAGATT TCTACCCAGC CAAGATCAAA GTGCGCTGGT
              TGTTGTGAGA CCAGACGAGT CACTGTCTAA AGATGGGTCG GTTCTAGTTT CACGCGACCA

R   N   G   Q   E   E   T   V   G   V   S   S   T   Q   L   I   R   N   G   D
    1381      TCCGGAATGG CCAGGAGGAG ACGGTGGGGG TCTCATCCAC ACAGCTTATT AGGAATGGGG
              AGGCCTTACC GGTCCTCCTC TGCCACCCCC AGAGTAGGTG TGTCGAATAA TCCTTACCCC

W   T   F   Q   V   L   V   M   L   E   M   T   P   R   R   G   E   V   Y   T
    1441      ACTGGACCTT CCAGGTCCTG GTCATGCTGG AGATGACCCC TCGGCGGGGA GAGGTCTACA
              TGACCTGGAA GGTCCAGGAC CAGTACGACC TCTACTGGGG AGCCGCCCCT CTCCAGATGT
```

FIG. 9A

```
           · C   H   V    E   H   P    S   L   K   S    P   I   T    V   E   W    R   A   Q   S ·
1501  CCTGTCACGT GGAGCATCCC AGCCTGAAGA GCCCCATCAC TGTGGAGTGG AGGGCACAGT
      GGACAGTGCA CCTCGTAGGG TCGGACTTCT CGGGGTAGTG ACACCTCACC TCCCGTGTCA

· E   S   A    W   S   K    G   G   G   G    G   G   G    G   R   I    A   R   L   E ·
1561  CTGAGTCTGC CTGGAGCAAG GGAGGCGGAG GCGGTGGCGG AGGACGGATC GCTCGGCTAG
      GACTCAGACG GACCTCGTTC CCTCCGCCTC CGCCACCGCC TCCTGCCTAG CGAGCCGATC

· E   K   V    K   T   L    K   A   Q   N    S   E   L    A   S   T    A   N   M   L ·
1621  AGGAAAAAGT GAAAACCTTG AAAGCGCAAA ACTCCGAGCT GGCGTCCACG GCCAACATGC
      TCCTTTTTCA CTTTTGGAAC TTTCGCGTTT TGAGGCTCGA CCGCAGGTGC CGGTTGTACG
                                                                  XhoI
                                                                  ~~~~~~~
                                                                      XbaI
                                                                      ~~~~~~
           · R   E   Q    V   A   Q    L   K   Q   K    V   M   N    H   *
1681  TCAGGGAACA GGTGGCACAG CTTAAGCAGA AAGTCATGAA CCACTGAGCTAGAG
      AGTCCCTTGT CCACCGTGTC GAATTCGTCT TTCAGTACTT GGTGACTCGATCTC
```

FIG. 9B

SEQUENCE LISTING

<160> NUMBER OF SEQ ID NOS: 19

<210> SEQ ID NO 1
<211> LENGTH: 12
<212> TYPE: PRT
<213> ORGANISM: Unknown
<220> FEATURE:
<223> OTHER INFORMATION: Description of Unknown: pMOG
      38-49 antigen peptide

<400> SEQUENCE: 1

Gly Trp Tyr Arg Ser Pro Phe Ser Arg Val Val His
1               5                   10

<210> SEQ ID NO 2
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Ile Ile Tyr Leu Ile Leu Leu Phe Thr Ala Val Arg Gly Gly
1               5                   10                  15

Trp Tyr Arg Ser Pro Phe Ser Arg Val Val His Gly Gly Gly Gly Ser
            20                  25                  30

Leu Val Pro Arg Gly Ser Gly Gly Gly Ser Gly Asp Ser Glu Arg
        35                  40                  45

His Phe Val Tyr Gln Phe Met Gly Glu Cys Tyr Phe Thr Asn Gly Thr
    50                  55                  60

Gln Arg Ile Arg Tyr Val Thr Arg Tyr Ile Tyr Asn Arg Glu Glu Tyr
65                  70                  75                  80

Val Arg Tyr Asp Ser Asp Val Gly Glu His Arg Ala Val Thr Glu Leu
                85                  90                  95

Gly Arg Pro Asp Ala Glu Tyr Trp Asn Ser Gln Pro Glu Ile Leu Glu
            100                 105                 110

Arg Thr Arg Ala Glu Leu Asp Thr Val Cys Arg His Asn Tyr Glu Gly
        115                 120                 125

Pro Glu Thr His Thr Ser Leu Arg Arg Leu Glu Gln Pro Asn Val Val
    130                 135                 140

Ile Ser Leu Ser Arg Thr Glu Ala Leu Asn His His Asn Thr Leu Val
145                 150                 155                 160

Cys Ser Val Thr Asp Phe Tyr Pro Ala Lys Ile Lys Val Arg Trp Phe
                165                 170                 175

Arg Asn Gly Gln Glu Glu Thr Val Gly Val Ser Ser Thr Gln Leu Ile
            180                 185                 190

Arg Asn Gly Asp Trp Thr Phe Gln Val Leu Val Met Leu Glu Met Thr
        195                 200                 205

Pro Arg Arg Gly Glu Val Tyr Thr Cys His Val Glu His Pro Ser Leu
    210                 215                 220

Lys Ser Pro Ile Thr Val Glu Trp Arg Ala Gln Ser Glu Ser Ala Trp
225                 230                 235                 240

Ser Lys Gly Gly Gly Gly Gly Gly Gly Arg Ile Ala Arg Leu Glu
                245                 250                 255

Glu Lys Val Lys Thr Leu Lys Ala Gln Asn Ser Glu Leu Ala Ser Thr
            260                 265                 270

Ala Asn Met Leu Arg Glu Gln Val Ala Gln Leu Lys Gln Lys Val Met

Asn His
     290

<210> SEQ ID NO 3
<211> LENGTH: 886
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (7)..(876)

<400> SEQUENCE: 3

```
ggtacc atg gct atc atc tac ctc atc ctc ctg ttc acc gct gtg cgg        48
       Met Ala Ile Ile Tyr Leu Ile Leu Leu Phe Thr Ala Val Arg
       1               5                  10 ggc ggc tgg tat aga agt cca ttt agc cgt gtt gtc cat gga ggt gga       96
Gly Gly Trp Tyr Arg Ser Pro Phe Ser Arg Val Val His Gly Gly Gly
15                  20                  25                  30 ggc tca cta gtg ccc cga ggc tct gga ggt gga ggc tct gga gac tcc      144
Gly Ser Leu Val Pro Arg Gly Ser Gly Gly Gly Gly Ser Gly Asp Ser
                35                  40                  45 gaa agg cat ttc gtg tac cag ttc atg ggc gag tgc tac ttc acc aac      192
Glu Arg His Phe Val Tyr Gln Phe Met Gly Glu Cys Tyr Phe Thr Asn
            50                  55                  60 ggg acg cag cgc ata cga tat gtg acc aga tac atc tac aac cgg gag      240
Gly Thr Gln Arg Ile Arg Tyr Val Thr Arg Tyr Ile Tyr Asn Arg Glu
        65                  70                  75 gag tac gtg cgc tac gac agc gac gtg ggc gag cac cgc gcg gtg acc      288
Glu Tyr Val Arg Tyr Asp Ser Asp Val Gly Glu His Arg Ala Val Thr
    80                  85                  90 gag ctg ggg cgg cca gac gcc gag tac tgg aac agc cag ccg gag atc      336
Glu Leu Gly Arg Pro Asp Ala Glu Tyr Trp Asn Ser Gln Pro Glu Ile
95                  100                 105                 110 ctg gag cga acg cgg gcc gag ctg gac acg gtg tgc aga cac aac tac      384
Leu Glu Arg Thr Arg Ala Glu Leu Asp Thr Val Cys Arg His Asn Tyr
                115                 120                 125 gag ggg ccg gag acc cac acc tcc ctg cgg cgg ctt gaa cag ccc aat      432
Glu Gly Pro Glu Thr His Thr Ser Leu Arg Arg Leu Glu Gln Pro Asn
            130                 135                 140 gtc gtc atc tcc ctg tcc agg aca gag gcc ctc aac cac cac aac act      480
Val Val Ile Ser Leu Ser Arg Thr Glu Ala Leu Asn His His Asn Thr
        145                 150                 155 ctg gtc tgc tca gtg aca gat ttc tac cca gcc aag atc aaa gtg cgc      528
Leu Val Cys Ser Val Thr Asp Phe Tyr Pro Ala Lys Ile Lys Val Arg
    160                 165                 170 tgg ttc cgg aat ggc cag gag gag acg gtg ggg gtc tca tcc aca cag      576
Trp Phe Arg Asn Gly Gln Glu Glu Thr Val Gly Val Ser Ser Thr Gln
175                 180                 185                 190 ctt att agg aat ggg gac tgg acc ttc cag gtc ctg gtc atg ctg gag      624
Leu Ile Arg Asn Gly Asp Trp Thr Phe Gln Val Leu Val Met Leu Glu
                195                 200                 205 atg acc cct cgg cgg gga gag gtc tac acc tgt cac gtg gag cat ccc      672
Met Thr Pro Arg Arg Gly Glu Val Tyr Thr Cys His Val Glu His Pro
            210                 215                 220 agc ctg aag agc ccc atc act gtg gag tgg agg gca cag tct gag tct      720
Ser Leu Lys Ser Pro Ile Thr Val Glu Trp Arg Ala Gln Ser Glu Ser
        225                 230                 235
```

```
gcc tgg agc aag gga ggc gga ggc ggt ggc gga gga cgg atc gct cgg    768
Ala Trp Ser Lys Gly Gly Gly Gly Gly Gly Gly Gly Arg Ile Ala Arg
240                 245                 250 cta gag gaa aaa gtg aaa acc ttg aaa gcg caa aac tcc gag ctg gcg    816
Leu Glu Glu Lys Val Lys Thr Leu Lys Ala Gln Asn Ser Glu Leu Ala
255                 260                 265                 270 tcc acg gcc aac atg ctc agg gaa cag gtg gca cag ctt aag cag aaa    864
Ser Thr Ala Asn Met Leu Arg Glu Gln Val Ala Gln Leu Lys Gln Lys
                275                 280                 285 gtc atg aac cac tgagctagag                                         886
Val Met Asn His
        290
```

<210> SEQ ID NO 4
<211> LENGTH: 21
<212> TYPE: PRT
<213> ORGANISM: Unknown
<220> FEATURE:
<223> OTHER INFORMATION: Description of Unknown: MOG
      35-55 peptide

<400> SEQUENCE: 4

```
Met Glu Val Gly Trp Tyr Arg Ser Pro Phe Ser Arg Val Val His Leu
1               5                   10                  15

Tyr Arg Asn Gly Lys
            20
```

<210> SEQ ID NO 5
<211> LENGTH: 20
<212> TYPE: PRT
<213> ORGANISM: Unknown
<220> FEATURE:
<223> OTHER INFORMATION: Description of Unknown: MOG
      36-55 peptide

<400> SEQUENCE: 5

```
Glu Val Gly Trp Tyr Arg Ser Pro Phe Ser Arg Val Val His Leu Tyr
1               5                   10                  15

Arg Asn Gly Lys
            20
```

<210> SEQ ID NO 6
<211> LENGTH: 9
<212> TYPE: PRT
<213> ORGANISM: Unknown
<220> FEATURE:
<223> OTHER INFORMATION: Description of Unknown: MAG
      287-295 peptide

<400> SEQUENCE: 6

```
Ser Leu Leu Leu Glu Leu Glu Glu Val
1               5
```

<210> SEQ ID NO 7
<211> LENGTH: 9
<212> TYPE: PRT
<213> ORGANISM: Unknown
<220> FEATURE:
<223> OTHER INFORMATION: Description of Unknown: MAG
      509-517 peptide

<400> SEQUENCE: 7

```
Leu Met Trp Ala Lys Ile Gly Pro Val
1               5
```

```
<210> SEQ ID NO 8
<211> LENGTH: 9
<212> TYPE: PRT
<213> ORGANISM: Unknown
<220> FEATURE:
<223> OTHER INFORMATION: Description of Unknown: MAG
      556-564 peptide

<400> SEQUENCE: 8

Val Leu Phe Ser Ser Asp Phe Arg Ile
1               5

<210> SEQ ID NO 9
<211> LENGTH: 9
<212> TYPE: PRT
<213> ORGANISM: Unknown
<220> FEATURE:
<223> OTHER INFORMATION: Description of Unknown: MBPI
      110-118 peptide

<400> SEQUENCE: 9

Ser Leu Ser Arg Phe Ser Trp Gly Ala
1               5

<210> SEQ ID NO 10
<211> LENGTH: 9
<212> TYPE: PRT
<213> ORGANISM: Unknown
<220> FEATURE:
<223> OTHER INFORMATION: Description of Unknown: MOG
      114-122 peptide

<400> SEQUENCE: 10

Lys Val Glu Asp Pro Phe Tyr Trp Val
1               5

<210> SEQ ID NO 11
<211> LENGTH: 10
<212> TYPE: PRT
<213> ORGANISM: Unknown
<220> FEATURE:
<223> OTHER INFORMATION: Description of Unknown: MOG
      166-175 peptide

<400> SEQUENCE: 11

Arg Thr Phe Asp Pro His Phe Leu Arg Val
1               5                   10

<210> SEQ ID NO 12
<211> LENGTH: 9
<212> TYPE: PRT
<213> ORGANISM: Unknown
<220> FEATURE:
<223> OTHER INFORMATION: Description of Unknown: MOG
      172-180 peptide

<400> SEQUENCE: 12

Phe Leu Arg Val Pro Cys Trp Lys Ile
1               5

<210> SEQ ID NO 13
<211> LENGTH: 10
<212> TYPE: PRT
<213> ORGANISM: Unknown
<220> FEATURE:
<223> OTHER INFORMATION: Description of Unknown: MOG
      179-188 peptide

<400> SEQUENCE: 13
```

```
Lys Ile Thr Leu Phe Val Ile Val Pro Val
1               5                   10

<210> SEQ ID NO 14
<211> LENGTH: 9
<212> TYPE: PRT
<213> ORGANISM: Unknown
<220> FEATURE:
<223> OTHER INFORMATION: Description of Unknown: MOG
      188-196 peptide

<400> SEQUENCE: 14

Val Leu Gly Pro Leu Val Ala Leu Ile
1               5

<210> SEQ ID NO 15
<211> LENGTH: 9
<212> TYPE: PRT
<213> ORGANISM: Unknown
<220> FEATURE:
<223> OTHER INFORMATION: Description of Unknown: MOG
      181-189 peptide

<400> SEQUENCE: 15

Thr Leu Phe Val Ile Val Pro Val Leu
1               5

<210> SEQ ID NO 16
<211> LENGTH: 10
<212> TYPE: PRT
<213> ORGANISM: Unknown
<220> FEATURE:
<223> OTHER INFORMATION: Description of Unknown: MOG
      205-214 peptide

<400> SEQUENCE: 16

Arg Leu Ala Gly Gln Phe Leu Glu Glu Leu
1               5                   10

<210> SEQ ID NO 17
<211> LENGTH: 9
<212> TYPE: PRT
<213> ORGANISM: Unknown
<220> FEATURE:
<223> OTHER INFORMATION: Description of Unknown: PLP
      80-88 peptide

<400> SEQUENCE: 17

Phe Leu Tyr Gly Ala Leu Leu Leu Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5

<210> SEQ ID NO 19
<211> LENGTH: 9
<212> TYPE: PRT
<213> ORGANISM: Unknown
```

```
<220> FEATURE:
<223> OTHER INFORMATION: Description of Unknown: IGRP
      206-214 peptide

<400> SEQUENCE: 19

Val Tyr Leu Lys Thr Asn Val Phe Leu
1               5
```

METHODS AND COMPOSITIONS FOR TREATING MULTIPLE SCLEROSIS AND RELATED DISORDERS

CROSS-REFERENCE TO RELATED APPLICATIONS

This application is a continuation of International Application No. PCT/IB2013/003033, filed Oct. 11, 2013, which in turn is a continuation-in-part of U.S. application Ser. No. 13/830,521, filed Mar. 14, 2013, and claims priority under 35 U.S.C. §119 (e) to U.S. Provisional Application No. 61/712,733, filed Oct. 11, 2012, the content of each of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on May 22, 2014, is named 378701-0610_SL.txt and is 11,284 bytes in size.

FIELD OF DISCLOSURE

This disclosure is directed to compositions and methods related to immunotherapy and medicine. In particular, this disclosure is related to therapeutics for the treatment of multiple sclerosis and related disorders.

BACKGROUND

Multiple sclerosis (MS) is a potentially debilitating disease in which the body's immune system eats away at the protective sheath that covers your nerves. This interferes with the communication between the brain and the rest of the body. Ultimately, this may result in deterioration of the nerves themselves, a process that is not reversible.

Statistics show that approximately 250,000 to 350,000 people in the United States have been diagnosed with this disease. Symptoms vary widely, depending on the amount of damage and which nerves are affected. People with severe cases of multiple sclerosis may lose the ability to walk or speak. Symptoms of MS include numbness in the arms or legs, pain, loss of vision, muscle weakness or tremors, paralysis, vertigo, fatigue, difficulty with speech, bladder dysfunction, depression, hearing loss, and itching.

There is no cure for MS, but certain medications have been found to ease MS attacks and possibly slow the disease. Treatments attempt to return function after an attack, prevent new attacks, and prevent disability. MS medications can have adverse effects or be poorly tolerated. Accordingly, there is a need in the art for better-tolerated, more effective therapies for MS.

SUMMARY

In response to a need in the art, described herein are therapeutic methods and compositions for treating or preventing multiple sclerosis or multiple sclerosis-related disorders. One aspect of the disclosure relates to a method for expanding and/or developing populations of anti-pathogenic autoreactive T-cells in a subject with multiple sclerosis or a multiple sclerosis-related disorder which method comprises, consists essentially of or yet further consists of administering to that subject an antigen-MHC-nanoparticle complex, wherein the antigen is a multiple sclerosis-related antigen.

A further aspect relates to a method for treating multiple sclerosis or a multiple sclerosis related disorder in a subject in need thereof comprising, consisting essentially of or yet further consisting of administering an effective amount of an antigen-MHC-nanoparticle complex to the subject, wherein the antigen is a multiple sclerosis-related antigen. Also provided is the use of an antigen-MHC-nanoparticle complex in the preparation of a medicament for the treatment of multiple sclerosis or for expanding and/or developing populations of anti-pathogenic autoreactive T-cells, wherein the antigen is a multiple sclerosis-related antigen.

Other aspects relate to a complex comprising, consisting essentially of or yet further consisting of, a nanoparticle; a MEW protein; and a multiple sclerosis-related antigen. Also provided are compositions comprising, consisting essentially of, or yet further consisting of, the antigen-MHC-nanoparticle as described herein and a carrier. Yet further aspects relate to kits comprising, consisting essentially of, or yet further consisting of the antigen-MHC-nanoparticle composistions described herein and instructions for use.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 9A-9B show the protein (SEQ ID NO: 2) and DNA (SEQ ID NO: 3) sequences of $pMOG_{36-55}$-I-Abeta (b)-C-Jun construct (SEQ ID NOS: 2-3, respectively, in order of appearance). The sequences of individual components in the fusion protein are HA leader (underlined) followed by pMOG$_{38-49}$-peptide sequence (double underlined), I-Abeta (b) (dotted underlined) and C-Jun (shaded) sequences. GS linkers are not highlighted. FIG. 9A depicts base pairs 849 through 1500 of SEQ ID NO: 3 and the first 216 amino acids of SEQ ID NO:2. FIG. 9B depicts base pairs 1501 through 1734 of SEQ ID NO: 3 and the final 74 amino acids of SEQ ID NO:2.

DETAILED DESCRIPTION

Figure 1:
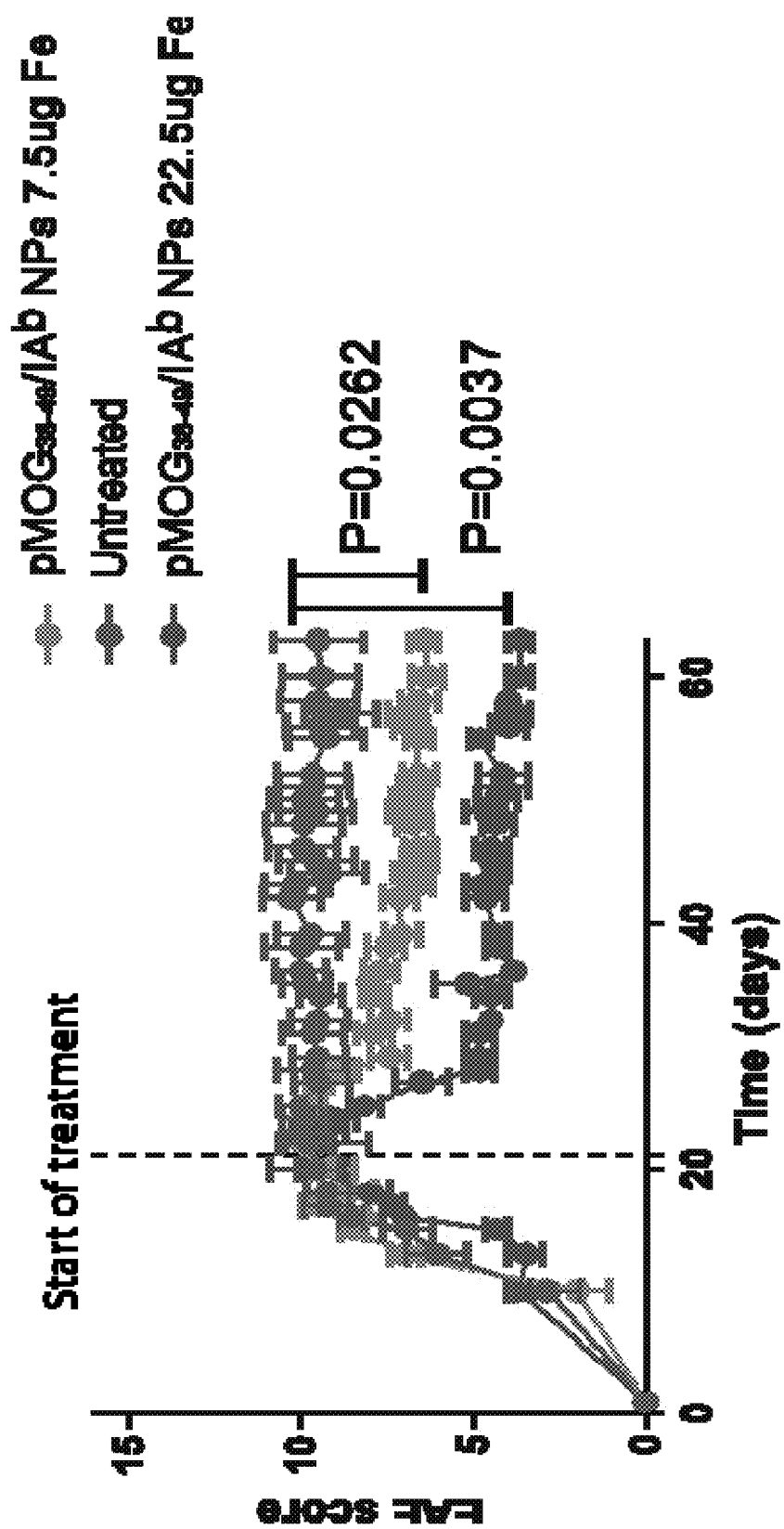
FIG. 1 shows that pMHC class II-NP therapy reduces the severity of established EAE in C57BL/6 mice. B6 mice were immunized with $pMOG_{35-55}$ in CFA and treated with pertussis toxin i.v. Mice were scored for signs of EAE using established criteria over a 15-point scale. Affected mice were treated with two weekly doses of 7.5-22.5 ug of $pMOG_{38-49}/IA^b$-coated NPs, beginning 21 days after immunization.
Figure 2:
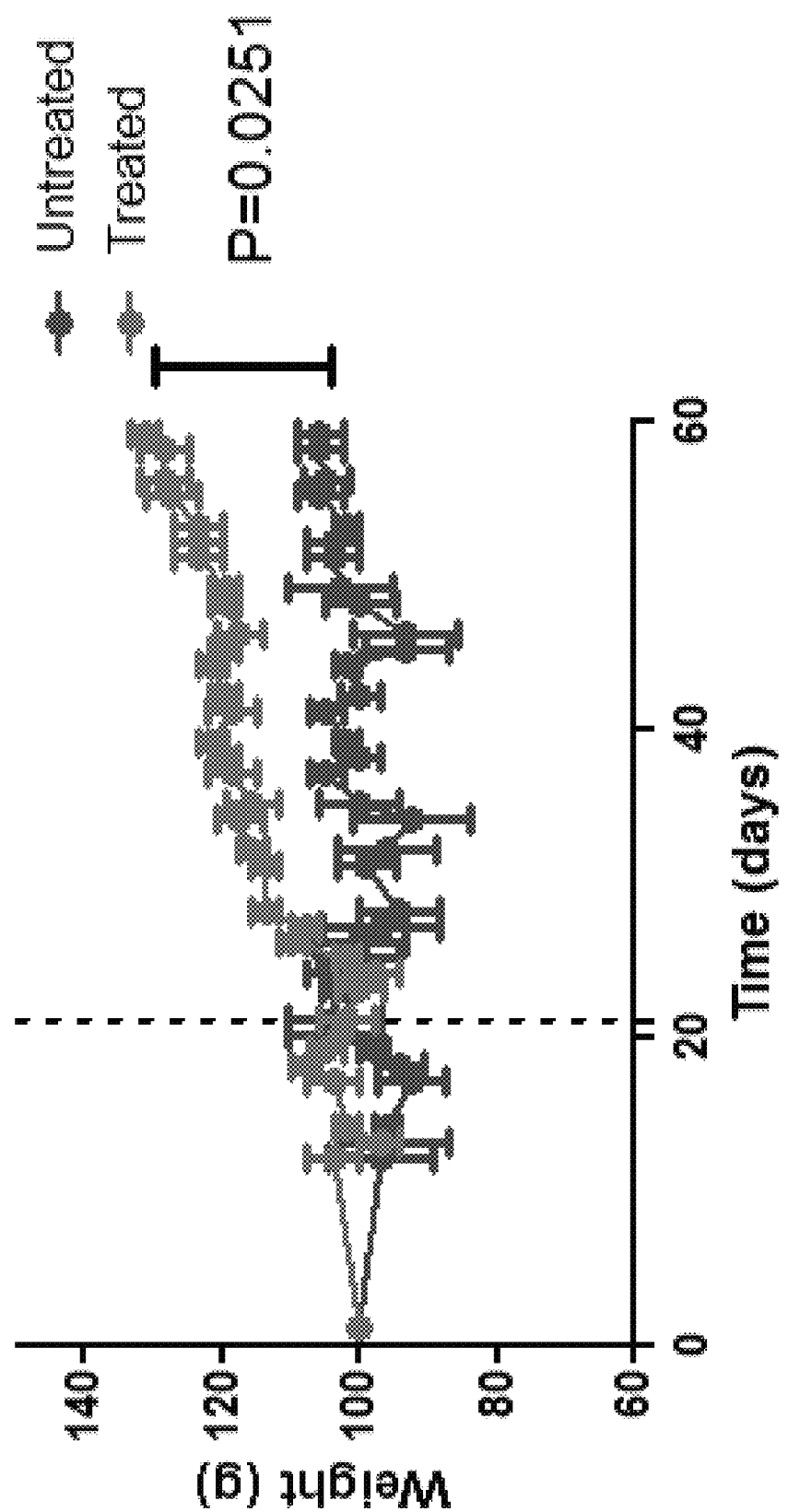
FIG. 2 demonstrates that mice with chronic EAE treated with pMHC class II-NP therapy ($pMOG_{38-49}$/I-$A^b$-coated NPs) have increased weight compared to the untreated EAE mice.
Figure 3:
FIG. 3 is a photograph of treated and untreated mice with EAE. Treated mice (NAVACIM) appear healthier than untreated mice.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients.

I. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention, such as compositions for treating or preventing multiple sclerosis. "Consisting of" shall mean excluding more than trace elements of other ingredients and substantial method steps. Embodiments defined by each of these transition terms are within the scope of this invention.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, will be used preferentially. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to nanoparticles made from materials which undergo bioabsorption in vivo over a period of time such that long term accumulation of the material in the patient is avoided. In a preferred embodiment, the biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the nanoparticles used in this invention. In one embodiment, iron oxide and a biocompatible, bioabsorbable polymer can be combined. For example, iron oxide and PGLA can be combined to form a nanoparticle.

An antigen-MHC-nanoparticle complex refers to presentation of a peptide, carbohydrate, lipid, or other antigenic segment, fragment, or epitope of an antigenic molecule or protein (i.e., self peptide or autoantigen) on a surface, such as a biocompatible biodegradable nanosphere. "Antigen" as used herein refers to all, part, fragment, or segment of a molecule that can induce an immune response in a subject or an expansion of anti-pathogenic cells.

The term "about" when used before a numerical designation, e.g., temperature, time, amount, and concentration, including range, indicates approximations which may vary by (+) or (−) 10%, 5%, or 1%.

A "mimic" is an analog of a given ligand or peptide, wherein the analog is substantially similar to the ligand. "Substantially similar" means that the analog has a binding profile similar to the ligand except the mimic has one or more functional groups or modifications that collectively accounts for less than about 50%, less than about 40%, less than about 30%, less than about 20%, less than about 10%, or less than about 5% of the molecular weight of the ligand.

Multiple sclerosis (MS) is also known as "disseminated sclerosis," "encephalomyelitis disseminate," or "allergic encephalomyelitis." MS is an inflammatory disease in which the fatty myelin sheaths around the axons of the brain and spinal cord are damaged, leading to demyelination and scarring as well as a broad spectrum of signs and symptoms. Multiple sclerosis-related disorders include, for example, neuromyelitis optica (NMO), uveitis, neuropathis pain, and the like.

"Myelin Oligodendrocyte Glycoprotein" (MOG) is a glycoprotein believed to be important in the process of myelinization of nerves in the central nervous system (CNS). In humans this protein is encoded by the MOG gene. It is speculated to serve as a necessary "adhesion molecule" to provide structural integrity to the myelin sheath and is known to develop late on the oligodendrocyte. The GenBank accession numbers NM_001008228.2 and NP_001008229.1 represent the mRNA and protein sequence, respectively, of the MOG gene. The sequence associated with each of these GenBank accession numbers is incorporated by reference for all purposes.

The term "anti-pathogenic autoreactive T cell" refers to a T cell with anti-pathogenic properties (i.e. T cells that counteract MS). These T cells can include anti-inflammatory T cells, effector T cells, memory T cells, low-avidity T cells, T helper cells, autoregulatory T cells, cytotoxic T cells, natural killer T cells, CD4+ T cells, CD8+ T cells and the like.

The term "anti-inflammatory T cell" refers to a T cell that promotes an anti-inflammatory response. The anti-inflammatory function of the T cell may be accomplished through production and/or secretion of anti-inflammatory proteins, cytokines, chemokines, and the like. Anti-inflammatory proteins are also intended to encompass anti-proliferative signals that suppress immune responses. Anti-inflammatory proteins include IL-4, IL-10, IL-13, IFN-α, TGF-β, IL-1ra, G-CSF, and soluble receptors for TNF and IL-6. In certain embodiments, administration of the antigen-MHC nanoparticle complex leads to expansion and or increased induction of anti-inflammatory T cells effective for treating multiple sclerosis. Accordingly, aspects of the disclosure relate to methods for treating, in a patient, inflammation associated with MS, the method comprising, consisting essentially of or yet further consisting of administering to that patient an antigen-MHC-nanoparticle complex, wherein the antigen is a multiple sclerosis-related antigen.

The term "IL-10" or "Interleukin-10" refers to a cytokine encoded by the IL-10 gene. The IL-10 sequence is represented by the GenBank Accession No.: NM_000572.2 (mRNA) and NP_000563.1 (protein).

The term "TGF-β" or "Transforming growth factor beta" refers to a protein that can have an anti-inflammatory effect. TGF-β is a secreted protein that exists in at least three isoforms called TGF-β1, TGF-β2 and TGF-β3. It was also the original name for TGF-β1, which was the founding member of this family. The TGF-β family is part of a superfamily of proteins known as the transforming growth factor beta superfamily, which includes inhibins, activin, anti-mullerian hormone, bone morphogenetic protein, decapentaplegic and Vg-1.

A "an effective amount" is an amount sufficient to achieve the intended purpose, non-limiting examples of such include: initiation of the immune response, modulation of the immune response, suppression of an inflammatory response and modulation of T cell activity or T cell populations. In one aspect, the effective amount is one that functions to achieve a stated therapeutic purpose, e.g., a therapeutically effective amount. As described herein in detail, the effective amount, or dosage, depends on the purpose and the composition, component and can be determined according to the present disclosure.

The use of the word "a" or "an" when used in conjunction with the term "comprising" in the claims and/or the specification may mean "one," but it is also consistent with the meaning of "one or more," "at least one," and "one or more than one."

By "nanosphere," "NP," or "nanoparticle" herein is meant a small discrete particle that is administered singularly or pluraly to a subject, cell specimen or tissue specimen as appropriate. In certain embodiments, the nanoparticles are substantially spherical in shape. In certain embodiments, the nanoparticle is not a liposome or viral particle. In further embodiments, the nanoparticle is solid. The term "substantially spherical," as used herein, means that the shape of the particles does not deviate from a sphere by more than about 10%. Various known antigen or peptide complexes of the invention may be applied to the particles. The nanoparticles of this invention range in size from about 1 nm to about 1 μm and, preferably, from about 1 nm to about 100 nm and in some aspects refers to the average or median diameter of a plurality of nanoparticles when a plurality of nanoparticles are intended. Smaller nanosize particles can be obtained, for example, by the process of fractionation whereby the larger particles are allowed to settle in an aqueous solution. The upper portion of the solution is then recovered by methods known to those of skill in the art. This upper portion is enriched in smaller size particles. The process can be repeated until a desired average size is generated.

The use of the term "or" in the claims is used to mean "and/or" unless explicitly indicated to refer to alternatives only or the alternatives are mutually exclusive, although the disclosure supports a definition that refers to only alternatives and "and/or."

As used herein the phrase "immune response" or its equivalent "immunological response" refers to the development of a cell-mediated response (mediated by antigen-specific T cells or their secretion products). A cellular immune response is elicited by the presentation of polypeptide epitopes in association with Class I or Class II MEW molecules, to activate antigen-specific CD4$^+$ T helper cells and/or CD8+ cytotoxic T cells. The response may also involve activation of other components.

The terms "inflammatory response" and "inflammation" as used herein indicate the complex biological response of vascular tissues of an individual to harmful stimuli, such as pathogens, damaged cells, or irritants, and includes secretion of cytokines and more particularly of pro-inflammatory cytokines, i.e. cytokines which are produced predominantly by activated immune cells and are involved in the amplification of inflammatory reactions. Exemplary pro-inflammatory cytokines include but are not limited to IL-1, IL-6, TNF-a, IL-17, IL21, IL23, and TGF-β. Exemplary inflammations include acute inflammation and chronic inflammation. Acute inflammation indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). Chronic inflammation indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be inhibited in the sense of the present disclosure by affecting and in particular inhibiting anyone of the events that form the complex biological response associated with an inflammation in an individual.

The terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Glenn E. Morris, Epitope Mapping Protocols (1996). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis., 170:1110-1119, 1994), by antigen-dependent killing (cytotoxic T lymphocyte assay, Tigges et al., J. Immunol., 156(10):3901-3910, 1996) or by cytokine secretion. The presence of a cell-mediated immunological response can be determined by proliferation assays (CD4$^+$ T cells) or CTL (cytotoxic T lymphocyte) assays.

Optionally, an antigen or preferably an epitope of an antigen, can be chemically conjugated to, or expressed as, a fusion protein with other proteins, such as MHC and MHC related proteins.

As used herein, the terms "patient" and "subject" are used synonymously and refer to a mammal. In some embodiments the patient is a human. In other embodiments the patient is a mammal commonly used in a laboratory such as a mouse, rat, simian, canine, feline, bovine, equine, or ovine.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It also is contemplated that a particular polypeptide from a given species may be encoded by nucleic acids containing natural variations that having slightly different nucleic acid sequences but, nonetheless, encode the same or substantially similar protein, polypeptide, or peptide.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

"Homology" or "identity" or "similarity" can also refer to two nucleic acid molecules that hybridize under stringent conditions.

As used herein, the terms "treating," "treatment" and the like are used herein to mean obtaining a desired pharmacologic and/or physiologic effect. The effect may be therapeutic in terms of a partial or complete cure for a disorder and/or adverse effect attributable to the disorder. In one aspect, treatment indicates a reduction in the signs of the disease using an established scale.

As used herein, the term "multiple sclerosis-related disorder" intends a disorder that co-presents with a susceptibility to MS or with MS. Non-limiting examples of such include neuromyelitis optica (NMO), uveitis, neuropathic pain clerosis, atherosclerosis, arteriosclerosis, sclerosis disseminata systemic sclerosis, spino-optical MS, primary progressive MS (PPMS), and relapsing remitting MS (RRMS), progressive systemic sclerosis, and ataxic sclerosis, IGRP, which is encoded by a gene (located on chromosome 2q28-32 that overlaps a T1D susceptibility locus, IDDM7 (2q31), has also been recently identified as a beta-cell autoantigen of potential relevance in human T1D. Two HLA-A*0201-binding epitopes of human IGRP (hIGRP$_{228-236}$ and hIGRP$_{265-273}$) are recognized by islet-associated CD8+ cells from murine MHC class I-deficient NOD mice expressing an HLA-A*0201 transgene. IGRP$_{206-214}$ comprises the antigenic peptide VYLKTNVFL (SEQ ID NO: 19).

To prevent intends to prevent a disorder or effect in vitro or in vivo in a system or subject that is predisposed to the disorder or effect.

A "composition" is intended to mean a combination of active agent and another compound or composition, inert (for example, a detectable agent or label) or active, such as an adjuvant. In certain embodiments, the composition does not contain an adjuvant.

A "pharmaceutical composition" is intended to include the combination of an active agent with a carrier, inert or active, making the composition suitable for diagnostic or therapeutic use in vitro, in vivo or ex vivo.

The term "functionally equivalent codon" is used herein to refer to codons that encode the same amino acid, such as the six codons for arginine or serine, and also refers to codons that encode biologically equivalent amino acids (see below Table).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACI |
| Valine | Val | V | GUA GUC GUG GUU |
| Tryptophan | Trp | W | UGG |
| Tyrosine | Tyr | Y | UAC UAU |

As used herein, a "protein" or "polypeptide" or "peptide" refers to a molecule comprising at least five amino acid residues.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Descriptive Embodiments

This disclosure is based on the discovery that nanoparticles coupled to MS-relevant antigen-MHC complexes reduce MS or encephalomyelitis (EAE) symptoms (Example 1).

II. METHODS

The methods as described herein comprise, or alternatively consist essentially of, or yet further consist of the administration of an effective amount of an antigen-MHC-nanoparticle complex to a cell, tissue or subject for the purpose of: (1) expanding and/or developing populations of anti-pathogenic (or anti-MS) autoreactive T-cells; and/or (2) treating or preventing multiple sclerosis or a multiple sclerosis-related disorder in a patient with multiple sclerosis or a multiple sclerosis-related disorder or in a patient susceptible to multiple sclerosis or a multiple sclerosis-related disorder, in one aspect without compromising systemic immunity. The antigen used in the complex is a multiple sclerosis-related antigen. Methods to determine and monitor the therapy are known in the art and briefly described herein. When delivered in vitro, administration is by contacting the composition with the tissue or cell by any appropriate method, e.g., by administration to cell or tissue culture medium and is useful as a screen to determine if the therapy is appropriate for an individual or to screen for alternative therapies to be used as a substitute or in combination with the disclosed compositions. When administered in vivo, administration is by systemic or local administration. In vivo, the methods can be practiced on a non-human animal to screen alternative therapies to be used as a substitute or in combination with the disclosed compositions prior to human administration. In a human or non-human mammal, they are also useful to treat the disease or disorder.

The methods require administration of an effective amount of a complex comprising, consisting essentially of or yet further consisting of, a nanoparticle; a MHC protein; and a multiple sclerosis-related antigen.

The MHC of the antigen-MHC-nanoparticle complex can be MHC I, MHC II, or non-classical MHC. MHC proteins are described herein. In one embodiment, the MHC of the antigen-MHC-nanoparticle complex is a MHC class I. In another embodiment, the MHC is a MHC class II. In other embodiments, the MHC component of the antigen-MHC-nanoparticle complex is MHC class II or a non-classical MHC molecule as described herein. In one aspect, the antigen comprises, or alternatively consists essentially of, or yet further consists of the polypeptide GWYRSPFSRVVH (SEQ ID NO: 1) or an equivalent of SEQ ID NO: 1. Additional antigens that can be used in this invention comprise polypeptides comprising, or alternatively consisting essentially of, or yet further consisting of the polypeptides of the group: MOG$_{35-55}$, MEVGWYRSPFSRVVH-LYRNGK (SEQ ID NO: 4); MOG$_{36-55}$, EVGWYRSPFSRVVHLYRNGK (SEQ ID NO: 5); MAG$_{287-295}$, SLLLELEEV (SEQ ID NO: 6); MAG$_{509-517}$, LMWAKIGPV (SEQ ID NO: 7); MAG$_{556-564}$, VLFSSDFRI (SEQ ID NO: 8); MBPI$_{110-118}$, SLSRFSWGA (SEQ ID NO:

9); MOG$_{114-122}$, KVEDPFYWV (SEQ ID NO: 10); MOG$_{166-175}$, RTFDPHFLRV (SEQ ID NO: 11); MOG$_{172-180}$, FLRVPCWKI (SEQ ID NO: 12); MOG$_{179-188}$, KITLFVIVPV (SEQ ID NO: 13); MOG$_{188-196}$, VLG-PLVALI (SEQ ID NO: 14); MOG$_{181-189}$, TLFVIVPVL (SEQ ID NO: 15); MOG$_{205-214}$, RLAGQFLEEL (SEQ ID NO: 16); PLP$_{80-88}$, FLYGALLLA (SEQ ID NO: 17), or an equivalent of each thereof, or combinations thereof.

The size of the nanoparticle can range from about 1 nm to about 1 μm. In certain embodiments, the nanoparticle is less than about 1 μm in diameter. In other embodiments, the nanoparticle is less than about 500 nm, less than about 400 nm, less than about 300 nm, less than about 200 nm, less than about 100 nm, or less than about 50 nm in diameter. In further embodiments, the nanoparticle is from about 1 nm to about 10 nm, 15 nm, 20 nm, 25 nm, 30 nm, 40 nm, 50 nm, 75 nm, or 100 nm in diameter. In specific embodiments, the nanoparticle is from about 1 nm to about 100 nm, about 1 nm to about 50 nm, about 1 nm to about 20 nm, or about 5 nm to about 20 nm.

The size of the complex can range from about 5 nm to about 1 μm. In certain embodiments, the complex is less than about 1 μm or alternatively less than 100 nm in diameter. In other embodiments, the complex is less than about 500 nm, less than about 400 nm, less than about 300 nm, less than about 200 nm, less than about 100 nm, or less than about 50 nm in diameter. In further embodiments, the complex is from about 10 nm to about 50 nm, or about 20 nm to about 75 nm, or about 25 nm to about 60 nm, or from about 30 nm to about 60 nm, or in one aspect about 55 nm.

Applicant has discovered that the density of the antigen-MHC complexes on the nanoparticle contributes to the therapeutic benefit. Thus, as disclosed herein the antigen-MHC nanoparticle complex can have a defined density in the range of from about 0.05 MHC molecules per 100 nm$^2$ of surface area of the nanoparticle, assuming at least 2 MEW, or alternatively at least 8, or alternatively at least 9, or alternatively at least 10, or alternatively at least 11, or alternatively at least 12, MEW complexed to the nanoparticle. In one aspect the complex has an density of MHC from about 0.01 MHC per 100 nm$^2$ (0.05 MHC/100 nm$^2$) to about 30 MHC/100 nm$^2$, or alternatively from 0.1 MHC/100 nm$^2$ to about 25 MHC/100 nm$^2$, or alternatively from about 0.3 MHC/100 nm$^2$ to about 25 MHC/100 nm$^2$, or alternatively from about 0.4 MHC/100 nm$^2$ to about 25 MHC/100 nm$^2$, or alternatively from about 0.5 MHC/100 nm$^2$ to about 20 MHC/100 nm$^2$, or alternatively from about, or alternatively from 0.6 MHC/100 nm$^2$ to about 20 MHC/100 nm$^2$, or alternatively from about 1.0 MHC/100 nm$^2$ to about 20 MHC/100 nm$^2$, or alternatively from about 5.0 MHC/100 nm$^2$ to about 20 MHC/100 nm$^2$, or alternatively from about 10.0 MHC/100 nm$^2$ to about 20 MHC/100 nm$^2$, or alternatively from about 15 MHC/100 nm$^2$ to about 20 MHC/100 nm$^2$, or alternatively at least about 0.5, or alternatively at least about 1.0, or alternatively at least about 5.0, or alternatively at least about 10.0, or alternatively at least about 15.0 MHC/100 nm$^2$. In one aspect, when 9 or at least 9 MEW are complexed to a nanoparticle, the density range is from about 0.3 MHC/100 nm$^2$ to about 20 MHC/100 nm$^2$.

In one of its method aspects, there is provided a method for accumulating anti-inflammatory T cells in a patient in need thereof. In a further embodiment, the T cell is a CD4+ or CD8+ T cell. In a related embodiment, the T cell secretes IL-10 or TGFβ. The method comprises, consists essentially of, or yet further consists of administering to a patient in need thereof on effective amount of the antigen-MHC nanoparticle complex as described herein.

In one embodiment, the methods described herein are for treating a multiple sclerosis-related disorder. The method comprises, consists essentially of, or yet further consists of administering to a patient in need thereof on effective amount of the antigen-MHC nanoparticle complex as described herein. In a related embodiment, the multiple sclerosis-related disorder is selected from the group consisting of neuromyelitis optica (NMO), uveitis, and neuropathis pain.

Details regarding modes of administration in vitro and in vivo are described within.

III. ANTIGEN-MHC-NANOPARTICLE COMPLEXES

Certain aspects relate to processes for producing MS antigen-specific medicaments that specifically treat MS without compromising systemic immunity. Example 2 describes the production of antigen-MHC-nanoparticle complexes. Antigen-MHC-nanoparticle complexes useful in this invention comprise a MS relevant antigen.

A. Polypeptides and Polynucleotides

Further aspects relate to an isolated or purified polypeptide comprising, or consisting essentially of, or yet further consisting of, the amino acid sequence of SEQ ID NO: 1 or a polypeptide having at least about 80% sequence identity, or alternatively at least 85%, or alternatively at least 90%, or alternatively at least 95%, or alternatively at least 98% sequence identity to SEQ ID NO: 1, or polypeptides encoded by polynucleotides having at about 80% sequence identity, or alternatively at least 85%, or alternatively at least 90%, or alternatively at least 95%, or alternatively at least 98% sequence identity to the polynucleotide encoding SEQ ID NO: 1 or its complement, or a polypeptide encoded by a polynucleotide that hybridizes under conditions of moderate to high stringency to a polynucleotide encoding SEQ ID NO: 1 or its complement. Also provided are isolated and purified polynucleotides encoding the polypeptide corresponding to SEQ ID NO: 1, at least about 80% sequence identify to SEQ ID NO: 1, or alternatively at least 85%, or alternatively at least 90%, or alternatively at least 95%, or alternatively at least 98% sequence identity to SEQ ID NO: 1 or an equivalent, or a polynucleotide that hybridizes under stringent conditions to the polynucleotide, its equivalent or its complement and isolated or purified polypeptides encoded by these polynucleotides. The polypeptides and polynucleotides can be combined with non-naturally occurring substances with which they are not associated with in nature, e.g., carriers, pharmaceutically acceptable carriers, vectors and MHC molecules, nanoparticles as known in the art and as described herein.

Antigens, including segments, fragments and other molecules derived from an antigenic species, including but not limited to peptides, carbohydrates, lipids or other molecules presented by classical and non-classical MHC molecules of the invention are typically complexed or operatively coupled to a MHC molecule or derivative thereof. Antigen recognition by T lymphocytes is major histocompatibility complex (MHC)-restricted. A given T lymphocyte will recognize an antigen only when it is bound to a particular MHC molecule. In general, T lymphocytes are stimulated only in the presence of self-MHC molecules, and antigen is recognized as fragments of the antigen bound to self MHC molecules. MHC restriction defines T lymphocyte specificity in terms of the antigen recognized and in terms of the MHC molecule that binds its antigenic fragment(s). In particular aspects certain antigens will be paired with certain MHC molecules or polypeptides derived there from.

The term "operatively coupled" or "coated" as used herein, refers to a situation where individual polypeptide (e.g., MHC) and antigenic (e.g., peptide) components are combined to form the active complex prior to binding at the target site, for example, an immune cell. This includes the situation where the individual polypeptide complex components are synthesized or recombinantly expressed and subsequently isolated and combined to form a complex, in vitro, prior to administration to a subject; the situation where a chimeric or fusion polypeptide (i.e., each discrete protein component of the complex is contained in a single polypeptide chain) is synthesized or recombinantly expressed as an intact complex. Typically, polypeptide complexes are added to the nanoparticles to yield nanoparticles with adsorbed or coupled polypeptide complexes having a ratio of number of molecules:number of nanoparticle ratios from about, at least about or at most about about 0.1, 0.5, 1, 3, 5, 7, 10, 15, 20, 25, 30, 35, 40, 50, 100, 125, 150, 175, 200, 225, 250, 275, 300, 325, 350, 375, 400, 425, 450, 475, 500, 600, 700, 800, 900, 1000, 1500 or more to:1, more typically 0.1:1, 1:1 to 50:1 or 300:1. The polypeptide content of the nanoparticles can be determined using standard techniques.

B. MHC Molecules

Intracellular and extracellular antigens present quite different challenges to the immune system, both in terms of recognition and of appropriate response. Presentation of antigens to T cells is mediated by two distinct classes of molecules MHC class I (MHC-I) and MHC class II (MHC-II) (also identified as "pMHC" herein), which utilize distinct antigen processing pathways. Peptides derived from intracellular antigens are presented to CD8$^+$ T cells by MHC class I molecules, which are expressed on virtually all cells, while extracellular antigen-derived peptides are presented to CD4$^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. In certain embodiments of the invention, a particular antigen is identified and presented in the antigen-MHC-nanoparticle complex in the context of an appropriate MHC class I or II polypeptide. In certain aspects, the genetic makeup of a subject may be assessed to determine which MHC polypeptide is to be used for a particular patient and a particular set of peptides. In certain embodiments, the MHC class 1 component comprises all or part of a HLA-A, HLA-B, HLA-C, HLA-E, HLA-F, HLA-G or CD-1 molecule. In embodiments wherein the MHC component is a MHC class II component, the MHC class II component can comprise all or a part of a HLA-DR, HLA-DQ, or HLA-DP.

Non-classical MHC molecules are also contemplated for use in MHC complexes of the invention. Non-classical MHC molecules are non-polymorphic, conserved among species, and possess narrow, deep, hydrophobic ligand binding pockets. These binding pockets are capable of presenting glycolipids and phospholipids to Natural Killer T (NKT) cells or certain subsets of CD8+ T-cells such as Qa1 or HLA-E-restricted CD8+ T-cells. NKT cells represent a unique lymphocyte population that co-express NK cell markers and a semi-invariant T cell receptor (TCR). They are implicated in the regulation of immune responses associated with a broad range of diseases.

C. Antigenic Components

Certain aspects of the invention include methods and compositions concerning antigenic compositions including segments, fragments, or epitopes of polypeptides, peptides, nucleic acids, carbohydrates, lipids and other molecules that provoke or induce an antigenic response, generally referred to as antigens. In particular, antigenic segments or fragments of antigenic determinants, which lead to the destruction of a cell via an autoimmune response, can be identified and used in making an antigen-MHC-nanoparticle complex described herein. Embodiments of the invention include compositions and methods for the modulation of an immune response in a cell or tissue of the body.

Polypeptides and peptides of the invention may be modified by various amino acid deletions, insertions, and/or substitutions. In particular embodiments, modified polypeptides and/or peptides are capable of modulating an immune response in a subject. In some embodiments, a wild-type version of a protein or peptide are employed, however, in many embodiments of the invention, a modified protein or polypeptide is employed to generate an antigen-MHC-nanoparticle complex. An antigen-MHC-nanoparticle complex can be used to generate an anti-inflammatory immune response, to modify the T cell population of the immune system (i.e., re-educate the immune system), and/or foster the recruitment and accumulation of anti-inflammatory T cells to a particular tissue. The terms described above may be used interchangeably herein. A "modified protein" or "modified polypeptide" or "modified peptide" refers to a protein or polypeptide whose chemical structure, particularly its amino acid sequence, is altered with respect to the wild-type protein or polypeptide. In some embodiments, a modified protein or polypeptide or peptide has at least one modified activity or function (recognizing that proteins or polypeptides or peptides may have multiple activities or functions). It is specifically contemplated that a modified protein or polypeptide or peptide may be altered with respect to one activity or function yet retains a wild-type activity or function in other respects, such as immunogenicity or ability to interact with other cells of the immune system when in the context of an MHC-nanoparticle complex.

Antigens of the invention include antigens related to multiple sclerosis. Such antigens include, for example, those disclosed in US Pat. App. No: 2012-0077686, and antigens derived from myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, and 2'3'-cyclic nucleotide 3'-phosphodiesterase. In certain embodiments, the antigen is derived from antigen is derived from Myelin Oligodendrocyte Glycoprotein (MOG). In a related embodiment, the antigen corresponds to a peptide having at least 80% identity to a peptide comprising the sequence of SEQ ID NO: 1 or a polypeptide encoded by a polynucleotide that hybridizes under conditions of moderate to high stringency to a polynucleotide that encodes a sequence of SEQ ID NO: 1 or one having at least about 80% sequence identity to a sequence of SEQ ID NO: 1 or a complement thereof.

In certain embodiments, the size of a protein or polypeptide (wild-type or modified), including any complex of a protein or peptide of interest and in particular a MHC-peptide fusion, may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. In certain aspects, 5, 6, 7, 8, 9, 10 or more contiguous amino acids, including derivatives thereof, and fragments of an antigen, such as those amino acid sequences disclosed and referenced herein, can be used as antigens. It is contemplated that polypeptides may be mutated by truncation, rendering them shorter than their corresponding wild-type form, but also they might be altered by fusing or conjugating a heterologous protein sequence with a particular function (e.g., for presentation as a protein complex, for enhanced immunogenicity, etc.).

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of autoantigenic epitopes and other polypeptides of these compositions can be substitutional, insertional, or deletion variants. A modification in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a nonpolar or uncharged amino acid, and vice versa.

Proteins of the invention may be recombinant, or synthesized in vitro. Alternatively, a recombinant protein may be isolated from bacteria or other host cell.

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

It is contemplated that in compositions of the invention, there is between about 0.001 mg and about 10 mg of total protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 µg/ml or mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be antigen-MHC-nanoparticle complex.

The present invention contemplates the administration of an antigen-MHC-nanoparticle complex to effect a treatment against MS or and/or inflammation associated with MS.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, Adv. Enzymol., 47:45-148, 1978; Chous and Fasman, Annu, Rev. Biochem., 47:251-276, 1978, Chou and Fasman, Biochemistry, 13(2):211-222, 1974; Chau and Fasman, Biochemistry, 13(2):222-245, 1974, Chou and Fasman, Biophys. J., 26(3):385-399, 1979). Any of these may be used, if desired, to supplement the teachings of Hopp in U.S. Pat. No. 4,554,101.

Molecules other than peptides can be used as antigens or antigenic fragments in complex with MHC molecules, such molecules include, but are not limited to carbohydrates, lipids, small molecules, and the like. Carbohydrates are major components of the outer surface of a variety of cells. Certain carbohydrates are characteristic of different stages of differentiation and very often these carbohydrates are recognized by specific antibodies. Expression of distinct carbohydrates can be restricted to specific cell types.

D. Substrates/Nanoparticles

In certain aspect, antigen/MHC complexes are operatively coupled to a substrate which can be bound covalently or non-covently to the substrate A substrate can be in the form of a nanoparticle that optionally comprises a biocompatible and/or bioabsorbable material. Accordingly, in one embodiment, the nanoparticle is biocompatible and/or bioabsorbable. A substrate can also be in the form of a nanoparticle such as those described previously in US Patent Pub. No.: 2009/0155292 which is herein incorporated by reference in its entirety, which in one aspect is not a liposome Nanoparticles can have a structure of variable dimension and known variously as a nanosphere, a nanoparticle or a biocompatible biodegradable nanosphere or a biocompatible biodegradable nanoparticle. Such particulate formulations containing an antigen/MHC complex can be formed by covalent or non-covalent coupling of the complex to the nanoparticle.

The nanoparticles typically consist of a substantially spherical core and optionally one or more layers. The core may vary in size and composition. In addition to the core, the nanoparticle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers, and for these functionalities the layer or layers may typically range in thickness from about 0.001 micrometers (1 nanometer) to about 10 micrometers or more (depending on the desired nanoparticle diameter), these layers typically being applied on the outer surface of the nanoparticle.

The compositions of the core and layers may vary. Suitable materials for the particles or the core include, but are not limited to polymers, ceramics, glasses, minerals, and the like. Examples include, but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference in its entirety. In certain embodiments, the compositions of the core and layers may vary provided that the nanoparticles are biocompatible and bioabsorbable. The core could be of homogeneous composition, or a composite of two or more classes of material depending on the properties desired. In certain aspects, metal nanospheres will be used. These metal nanoparticles can be formed from Fe, Ca, Ga and the like. In certain embodiments, the nanoparticle comprises a core comprising metal or metal oxide.

As previously stated, the nanoparticle may, in addition to the core, include one or more layers. The nanoparticle may include a layer consisting of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxalkanoate)s of the PHB-PHV class; and other modified poly(saccharides) such as starch, cellulose and chitosan. Additionally, the nanoparticle may include a layer with suitable surfaces for attaching chemical functionalities for chemical binding or coupling sites.

Layers can be produced on the nanoparticles in a variety of ways known to those skilled in the art. Examples include sol-gel chemistry techniques such as described in Iler, Chemistry of Silica, John Wiley & Sons, 1979; Brinker and Scherer, Sol-gel Science, Academic Press, (1990). Additional approaches to producing layers on nanoparticles include surface chemistry and encapsulation techniques such as described in Partch and Brown, J. Adhesion, 67:259-276, 1998; Pekarek et al., Nature, 367:258, (1994); Hanprasopwattana, Langmuir, 12:3173-3179, (1996); Davies, Advanced Materials, 10:1264-1270, (1998); and references therein. Vapor deposition techniques may also be used; see for example Golman and Shinohara, Trends Chem. Engin., 6:1-6, (2000); and U.S. Pat. No. 6,387,498. Still other approaches include layer-by-layer self-assembly techniques such as described in Sukhorukov et al., Polymers Adv. Tech., 9(10-11):759-767, (1998); Caruso et al., Macromolecules, 32(7):2317-2328, (1998); Caruso et al., J. Amer. Chem. Soc., 121(25):6039-6046, (1999); U.S. Pat. No. 6,103,379 and references cited therein.

Nanoparticles may be formed by contacting an aqueous phase containing the antigen/MHC/co-stimulatory molecule complex and a polymer and a nonaqueous phase followed by evaporation of the nonaqueous phase to cause the coalescence of particles from the aqueous phase as taught in U.S. Pat. No. 4,589,330 or 4,818,542. Preferred polymers for such preparations are natural or synthetic copolymers or polymers selected from the group consisting of gelatin agar, starch, arabinogalactan, albumin, collagen, polyglycolic acid, polylactic acid, glycolide-L(−) lactide poly(episilon-caprolactone, poly(epsilon-caprolactone-CO-lactic acid), poly(epsilon-caprolactone-CO-glycolic acid), poly(β-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic acid, glycolide-L(−) lactide poly(episilon-caprolactone, poly(epsilon-caprolactone-CO-lactic acid), and poly(epsilon-caprolactone-CO-glycolic acid. Solvents useful for dissolving the polymer include: water, hexafluoroisopropanol, methylenechloride, tetrahydrofuran, hexane, benzene, or hexafluoroacetone sesquihydrate.

The size of the nanoparticle can range from about 1 nm to about 1 μm. In certain embodiments, the nanoparticle is less than about 1 μm in diameter. In other embodiments, the nanoparticle is less than about 500 nm, less than about 400 nm, less than about 300 nm, less than about 200 nm, less than about 100 nm, or less than about 50 nm in diameter. In further embodiments, the nanoparticle is from about 1 nm to about 10 nm, 15 nm, 20 nm, 25 nm, 30 nm, 40 nm, 50 nm, 75 nm, or 100 nm in diameter. In specific embodiments, the nanoparticle is from about 1 nm to about 100 nm, about 1 nm to about 50 nm, about 1 nm to about 20 nm, or about 5 nm to about 20 nm.

The size of the complex can range from about 5 nm to about 1 μm. In certain embodiments, the complex is less than about 1 μm or alternatively less than 100 nm in diameter. In other embodiments, the complex is less than about 500 nm, less than about 400 nm, less than about 300 nm, less than about 200 nm, less than about 100 nm, or less than about 50 nm in diameter. In further embodiments, the complex is from about 10 nm to about 50 nm, or about 20 nm to about 75 nm, or about 25 nm to about 60 nm, or from about 30 nm to about 60 nm, or in one aspect about 55 nm.

E. Coupling Antigen-MHC Complex with the Nanoparticle

In order to couple the substrate or nanospheres to the antigen-MHC complexes the following techniques can be applied.

The binding can be generated by chemically modifying the substrate or nanoparticle which typically involves the generation of "functional groups" on the surface, said functional groups being capable of binding to an antigen-MHC complex, and/or linking the optionally chemically modified surface of the substrate or nanoparticle with covalently or non-covalently bonded so-called "linking molecules," followed by reacting the antigen-MHC complex with the nanoparticles obtained.

The term "linking molecule" means a substance capable of linking with the substrate or nanoparticle and also capable of linking to an antigen-MHC complex. In certain embodiments, the antigen-MHC complexes are coupled to the nanoparticle by a linker. Non-limiting examples of suitable linkers include dopamine (DPA)-polyethylene glycol (PEG) linkers such as DPA-PEG-NHS ester, DPA-PEG-orthopyridyl-disulfide (OPSS) and/or DPA-PEG-Azide. Other linkers include peptide linkers, ethylene glycol, biotin, and strepdavidin.

The term "functional groups" as used herein before is not restricted to reactive chemical groups forming covalent bonds, but also includes chemical groups leading to an ionic interaction or hydrogen bonds with the antigen-MHC complex. Moreover, it should be noted that a strict distinction between "functional groups" generated at the surface and linking molecules bearing "functional groups" is not possible, since sometimes the modification of the surface requires the reaction of smaller linking molecules such as ethylene glycol with the nanosphere surface.

The functional groups or the linking molecules bearing them may be selected from amino groups, carbonic acid groups, thiols, thioethers, disulfides, guanidino, hydroxyl groups, amine groups, vicinal dioles, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or nanoparticle. Nucleic acids can provide a link to affinity molecules containing themselves nucleic acid molecules, though with a complementary sequence with respect to the linking molecule.

A specific example of a covalent linker includes poly(ethylene) glycol (PEG). The PEG linker may be a thiol-PEG-NH$_2$ linker.

In certain embodiments, the linker as described herein has a defined size. In some embodiments, the linker is less that about 10 kD, less than about 5 kD, less than about 4.5 kD, less than about 4 kD, less than about 3.5 kD, less than about 3 kD, less than about 2.5 kD, less than about 2 kD, or less than about 1 kD. In further embodiments, the linker is from about 0.5 kD to about 5, 4.5, 4, 3.5, 3, 2.5, 2, 1.5, or 1 kD. In yet further embodiments, the linker is from about 1 to about, 4.5, 4, 3.5, 3, 2.5, 2, or 1.5 kD.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

The surface of the substrate or nanoparticle can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction. This binding reaction can be performed with substrate or nanosphere as directly obtained from the preparation process or after a pre-treatment (for instance with trimethylsilyl bromide). In the first case the phosphonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or nanosphere involves heating in a diole such as ethylene glycol. It should be noted that this treatment may be redundant if the synthesis already proceeded in a diole. Under these circumstances the synthesis product directly obtained is likely to show the necessary functional groups. This treatment is however applicable to substrate or nanoparticle that were produced in N- or P-containing complexing agents. If such substrate or particle are subjected to an after-treatment with ethylene glycol, ingredients of the reaction medium (e.g. complexing agent) still binding to the surface can be replaced by the diole and/or can be dealkylated.

It is also possible to replace N-containing complexing agents still bound to the particle surface by primary amine derivatives having a second functional group. The surface of the substrate or nanoparticle can also be coated with silica. Silica allows a relatively simple chemical conjugation of organic molecules since silica easily reacts with organic linkers, such as triethoxysilane or chlorosilane. The nanoparticle surface may also be coated by homo- or copolymers. Examples for polymerizable coupling agents are. N-(3-aminopropyl)-3-mercaptobenzamidine, 3-(trimethoxysilyl) propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or nanoparticles containing oxidic transition metal compounds is conversion of the oxidic transition metal compounds by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance-via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or nanosphere surface are particularly suitable. Examples for linking molecules which can be non-covalently linked to core/shell nanospheres involve anionic, cationic or zwitter-ionic surfactants, acid or basic proteins, polyamines, polyamides, polysulfone or polycarboxylic acid. The hydrophobic interaction between substrate or nanosphere and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or nanoparticle can also be based on non-covalent, self-organising bonds. One example thereof involves simple detection probes with biotin as linking molecule and avidin- or strepdavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or nanosphere or thereafter. Further, it is possible, by means of incubation, to effect a direct binding of molecules to correspondingly pre-treated substrate or nanoparticle (for instance by trimethylsilyl bromide), which display a modified surface due to this pre-treatment (for instance a higher charge or polar surface).

F. Protein Production

The present invention describes polypeptides, peptides, and proteins for use in various embodiments of the present invention. For example, specific peptides and their complexes are assayed for their abilities to elicit or modulate an immune response. In specific embodiments, all or part of the peptides or proteins of the invention can also be synthesized in solution or on a solid support in accordance with conventional techniques. Various automatic synthesizers are commercially available and can be used in accordance with known protocols. See, for example, Stewart and Young, Solid Phase Peptide Synthesis, $2^{nd}$. Ed., Pierce Chemical Co.l, (1984); Tam et al., J. Am. Chem. Soc., 105:6442, (1983); Merrifield, Science, 232(4748):341-347, (1986); and Barany and Merrifield, The Peptides, Gross and Meinhofer (Eds.), Academic Press, NY, 1-284, (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are known to one skilled in the art and are briefly discussed herein. Examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

G. Nucleic Acids

The present invention may include recombinant polynucleotides encoding the proteins, polypeptides, peptides of the invention, such as, for example, SEQ ID NO: 1 or 2.

In particular embodiments, the invention concerns isolated nucleic acid segments and recombinant vectors incorporating nucleic acid sequences that encode an autoantigen and/or a MHC molecule. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

IV. PHARMACEUTICAL COMPOSITIONS AND ADMINISTRATION

Provided herein are pharmaceutical compositions useful for the treatment of disease.

A. Pharmaceutical Compositions

The antigen-MHC nanoparticle complexes can be administered alone or in combination with a carrier, such as a pharmaceutically acceptable carrier in a composition. Compositions of the invention may be conventionally administered parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. The preparation of an aqueous composition that contains a antigen-MHC-nanoparticle complex that modifies the subject's immune condition will be known to those of skill in the art in light of the present disclosure. In certain embodiments, a composition may be inhaled (e.g., U.S. Pat. No. 6,651,655, which is specifically incorporated by reference in its entirety). In one embodiment, the antigen-MHC-nanoparticle complex is administered systemically.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms antigen-MHC-nanoparticle complex per administration. Suitable regimes for initial administration and boosters are also variable, but are typified by an initial administration followed by subsequent administrations.

In many instances, it will be desirable to have multiple administrations of a peptide-MHC-nanoparticle complex, about, at most about or at least about 3, 4, 5, 6, 7, 8, 9, 10 or more. The administrations will normally range from 2 day to twelve week intervals, more usually from one to two week intervals. Periodic boosters at intervals of 0.5-5 years, usually two years, may be desirable to maintain the condition of the immune system. The course of the administrations may be followed by assays for inflammatory immune responses and/or autoregulatory T cell activity.

In some embodiments, pharmaceutical compositions are administered to a subject. Different aspects of the present invention involve administering an effective amount of a antigen-MHC-nanoparticle complex composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier may be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization. Sterilization of the solution will be done in such a way as to not diminish the therapeutic properties of the antigen-MHC-nanoparticle complex. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterilized solution thereof. One such method of sterilization of the solution is sterile filtration, however, this invention is meant to include any method of sterilization that does not significantly decrease the therapeutic properties of the antigen-MHC-nanoparticle complexes. Methods of sterilization that involve intense heat and pressure, such as autoclaving, may compromise the tertiary structure of the complex, thus significantly decreasing the therapeutic properties of the antigen-MHC-nanoparticle complexes.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

B. Combination Therapy

The compositions and related methods of the present invention, particularly administration of a antigen-MHC-nanoparticle complex, may also be used in combination with the administration of traditional therapies. These include, but are not limited to, Avonex (interferon beta-la), Betaseron (interferon beta-lb), Copaxone (glatiramer acetate), Novantrone (mitoxantrone), Rebif (interferon beta-la), Tysabri (natalizumab), Gilenya (fingolimod), Glatiramer, steroids, Cytoxan, Imuran, Baclofen, deep brain stimulation, Ampyra (dalfampridine), acupuncture, and physical therapy.

When combination therapy is employed, various combinations may be employed, for example antigen-MHC-nanoparticle complex administration is "A" and the additional agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the peptide-MHC complex compositions of the present invention to a patient/subject will follow general protocols for the administration of such compounds, taking into account the toxicity, if any. It is expected that the treatment cycles would be repeated as necessary. It also is contemplated that various standard therapies, such as hydration, may be applied in combination with the described therapy.

C. In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present invention, the compositions may be administered either in vitro, ex vivo, or in vivo. In certain in vitro embodiments, autologous T cells are incubated with compositions of this invention. The cells or tissue can then be used for in vitro analysis, or alternatively for ex vivo administration.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the invention. Changes therein and other uses which are encompassed within the spirit of the invention as defined by the scope of the claims will occur to those skilled in the art.

Example 1. pMHC Class II-NPs in Chronic EAE Autoimmune Disease Model

This example describes the use of nanoparticles coated with MS-related antigen-MHC complexes to treat EAE in an EAE mouse model. This novel therapeutic approach can be used for systemic delivery of nanoparticles coated with single MS-relevant peptideMHC complexes (pMHC) (i.e. one pMHC complex per disease). This discovery enables the rational design of disease-specific 'nanovaccines' capable of blunting autoimmunity without impairing systemic immunity, a long sought-after goal in the therapy of these disorders. FIG. 1 shows that monospecific, MS-relevant pMHC class II coated nanovaccines can reverse established experimental allergic encephalomyelitis (EAE) in both C57BL/6 mice. This approach is also applicable to human pMHC complexes known to be targeted by autoreactive CD4+

T-cells in MS patients. Demonstration of clinical efficacy in these pre-clinical models will pave the way for clinical trials in humans and, potentially, development of a cure for MS.

EAE requires the generation of autoreactive CD4+ cells along with the breakdown of the bloodbrain barrier, which enables the recruitment of encephalitogenic cells to the CNS. Immunization of C57BL/6 (B6) mice with pMOG$_{36-55}$ (200 μg) in CFA supplemented with 10 μg/ml *Mycobacterium tuberculosis* s.c. (at the base of the tail) along with 300 ng of Pertussis toxin i.p., followed by another dose of Pertussis toxin on day 2, induces a form of chronic EAE (>60 days) in all the animals that get sick (~70% in our colony).

Figure 4:
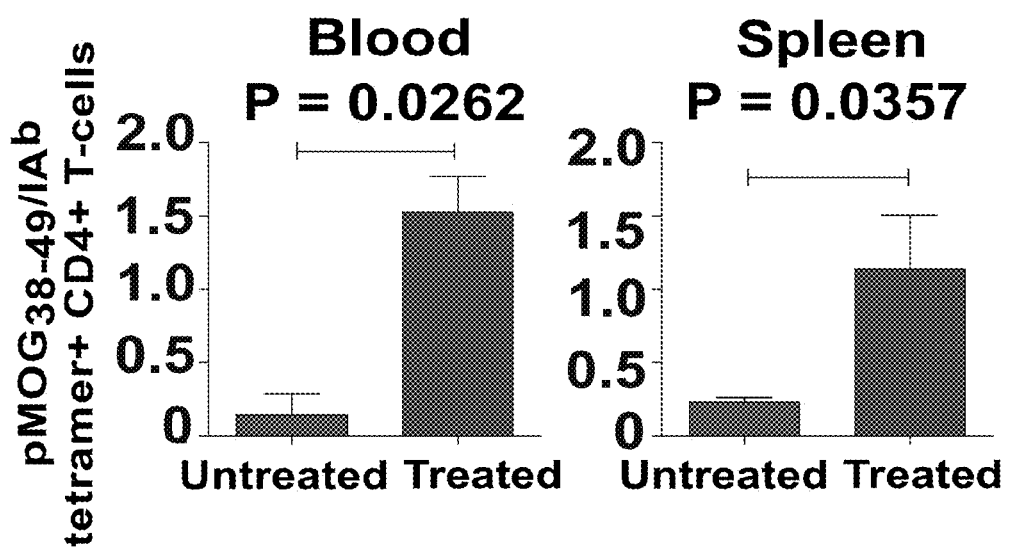
FIG. 4 shows the systemic expansion of cognate autoregulatory CD4+ T-cells by $pMOG_{38-49}/IA^b$-coated NPs in EAE-affected C57BL/6 mice. The magnitude of expansion in this model is comparable to that seen in NOD mice treated with type 1 diabetes-relevant pMHC class II-coated NPs (See, for example, U.S. Pat. No. 8,354,110, which is herein incorporated by reference in its entirety.
Figure 5:
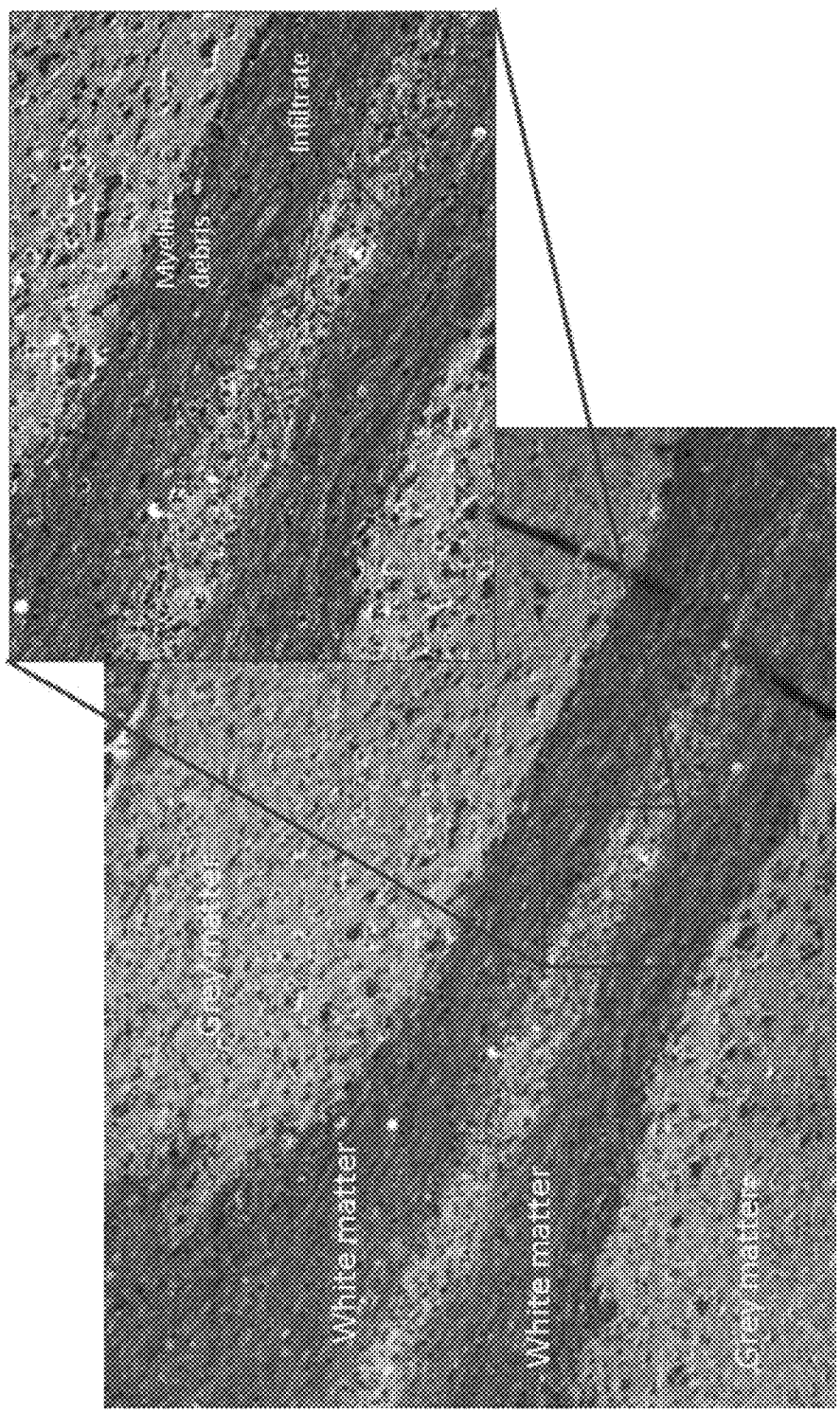
FIG. 5 depicts the spinal cords of untreated mice. The untreated mice displayed significant demyelination and dense mononuclear cell infiltrates of the white matter.
Figure 6:
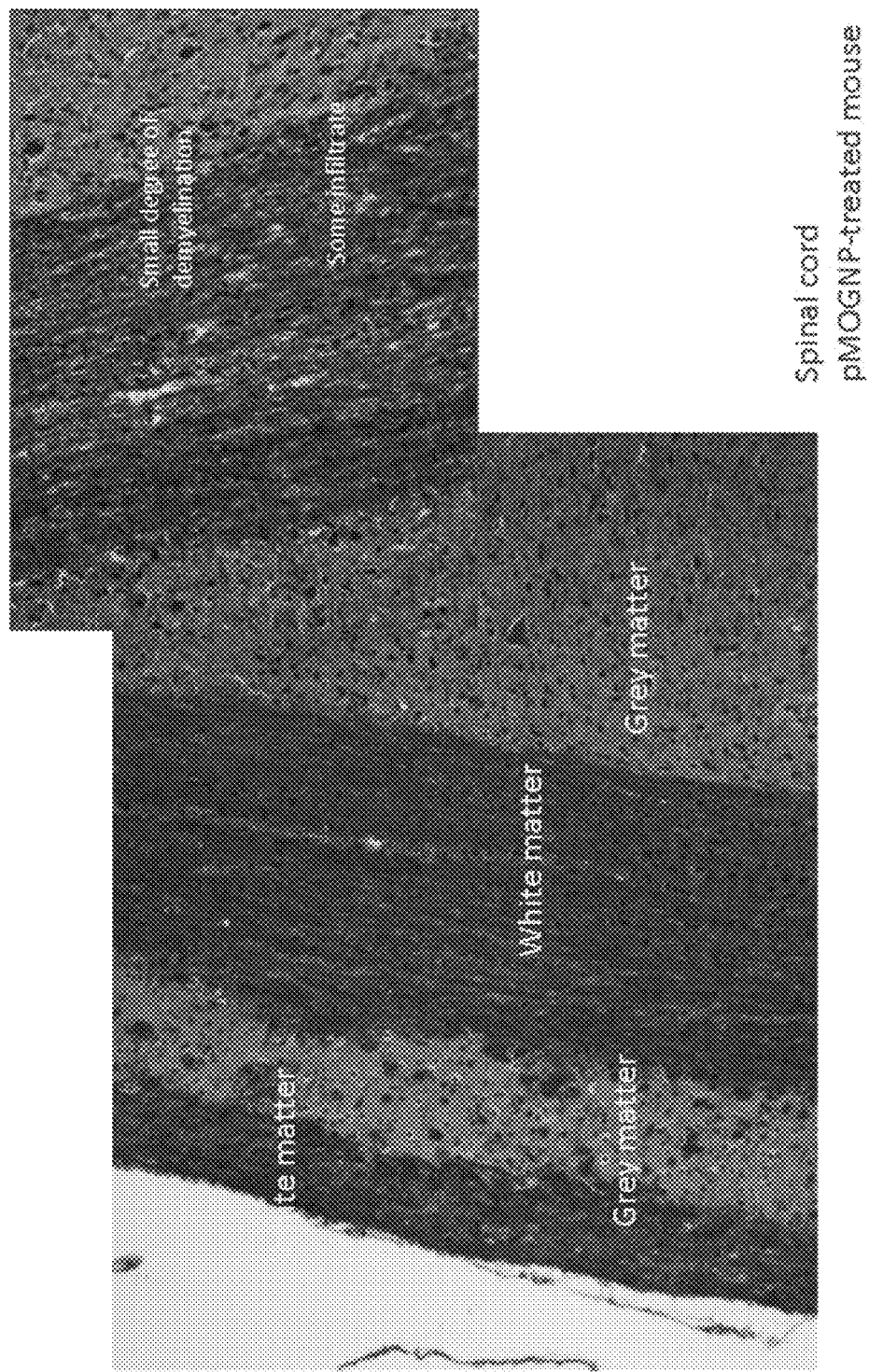
FIG. 6 depicts the spinal cords of mice treated with $pMOG_{38-49}/IA^b$-NPs. pMHC-NP-treated mice had significantly less demyelination and mononuclear cell infiltrates.
Figure 7:
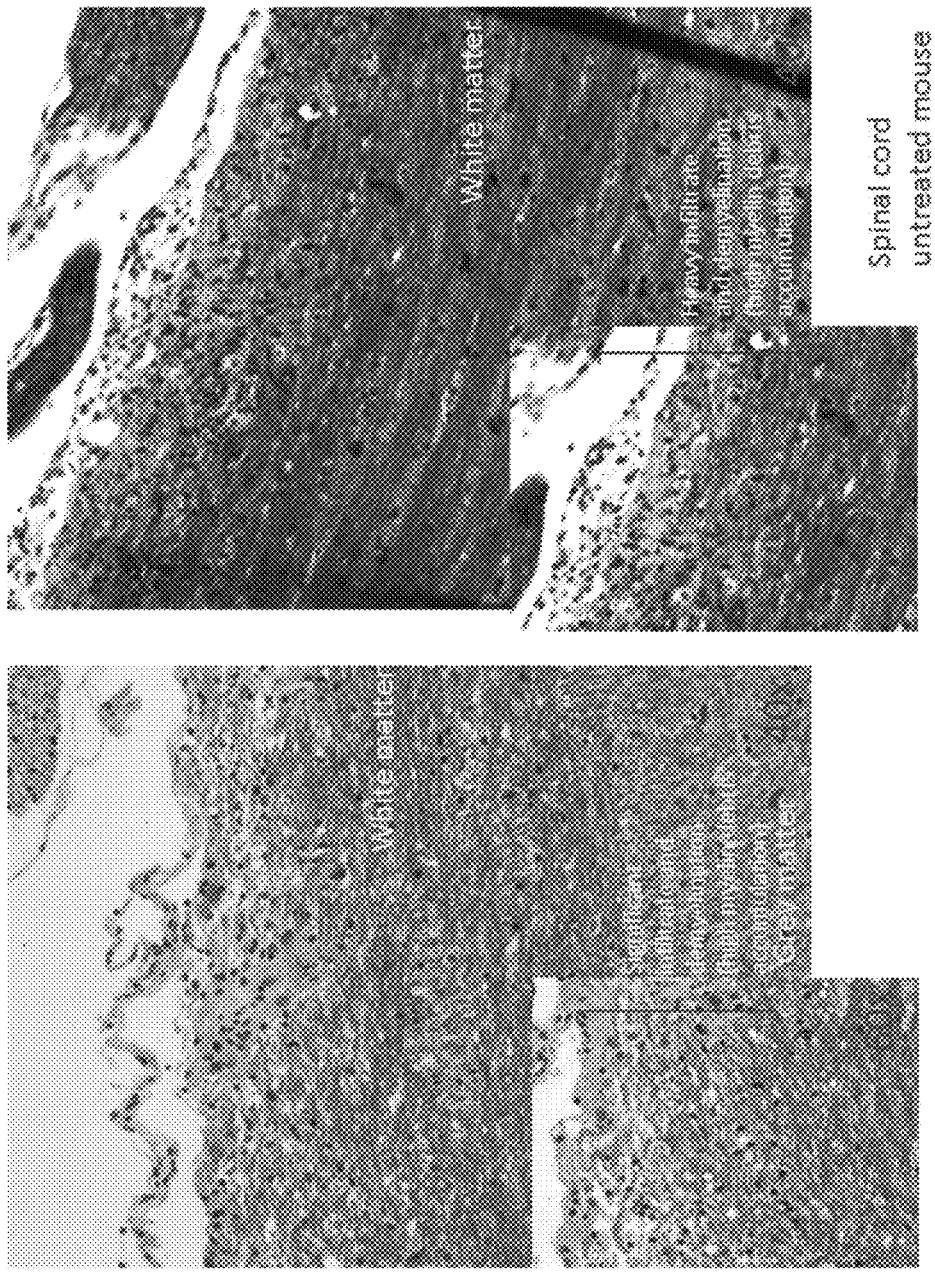
FIG. 7 shows representative examples for the spinal cord edges of 2 untreated EAE mice.
Figure 8:
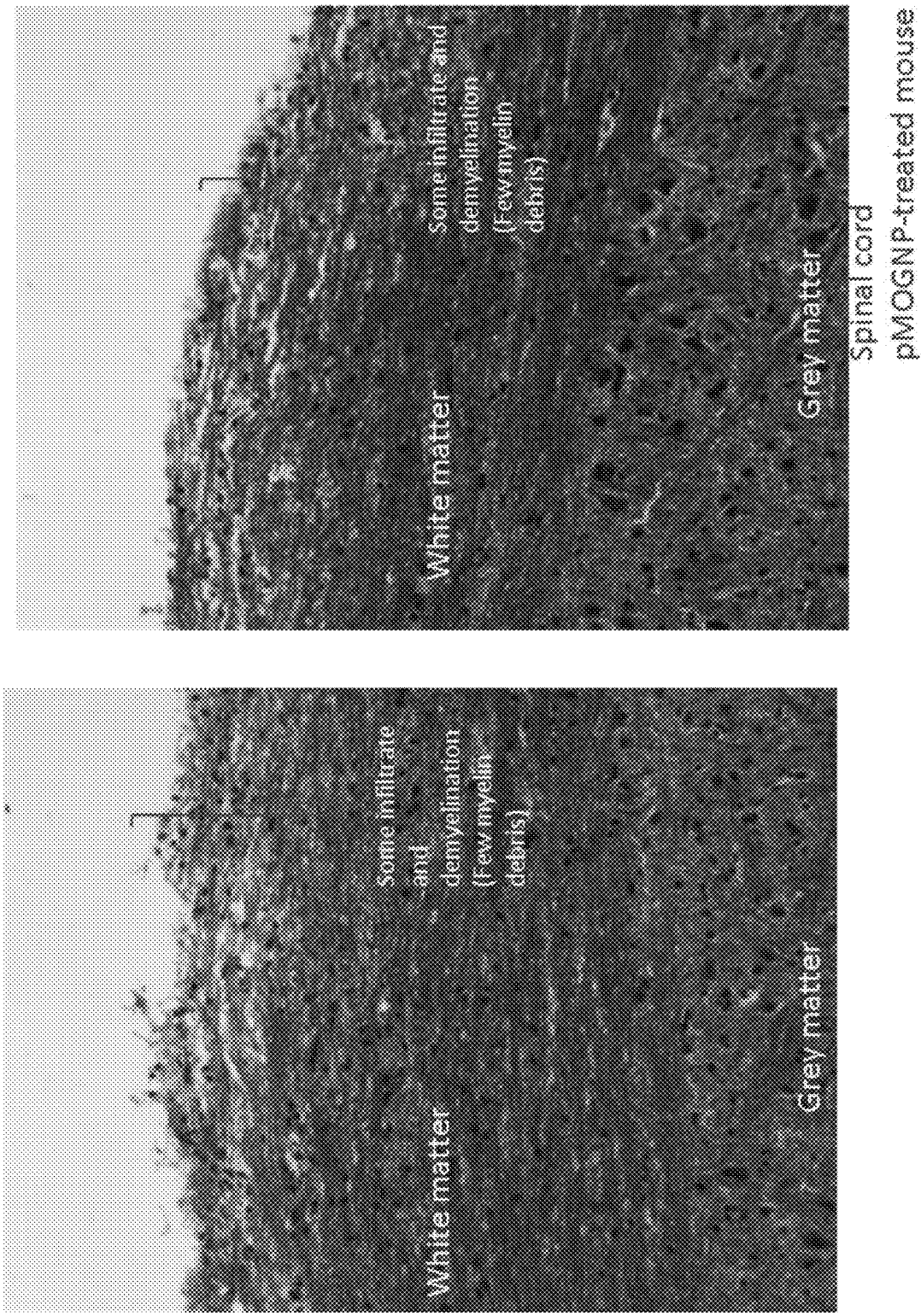
FIG. 8 shows representative examples for the spinal cord edges of 2 EAE mice treated with $pMOG_{38-49}/IA^b$-NPs. pMHC-NP-treated mice have significantly less demyelination as well as lower mononuclear cell infiltration.
Figure 10:
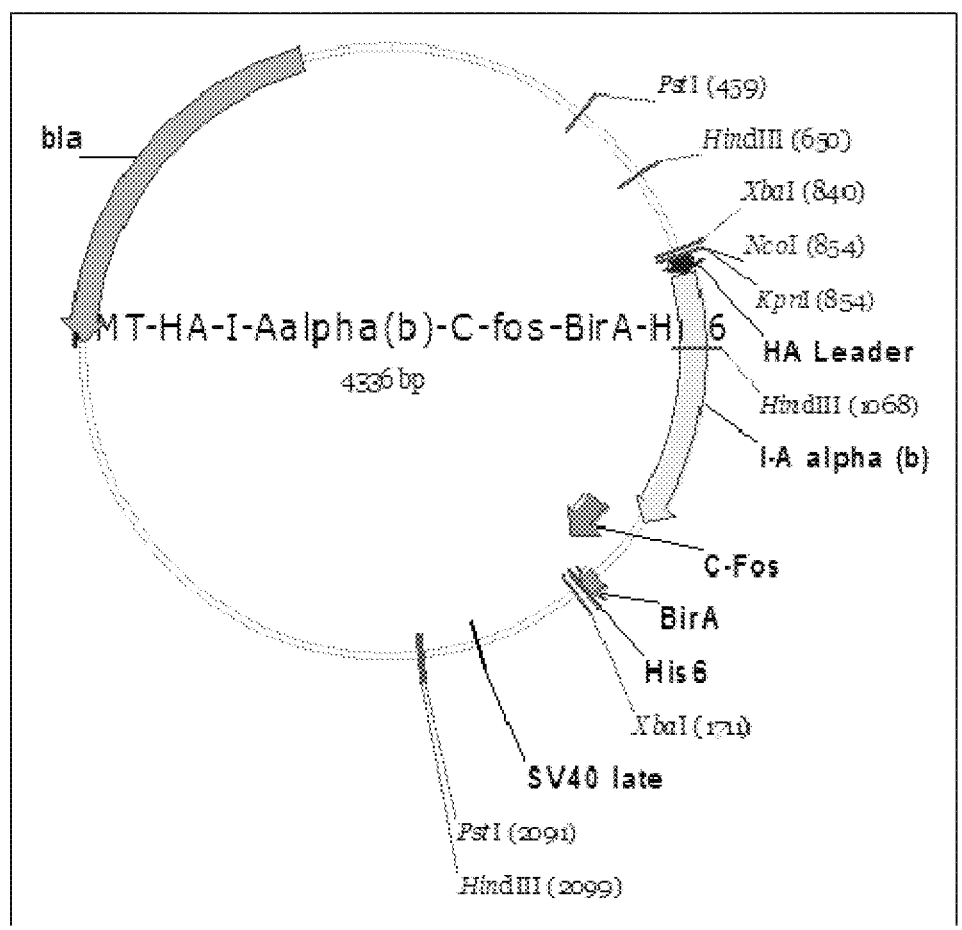
FIG. 10 is a DNA map of the antigen-containing vector. DNA construct sites encoding HA leader-I-Aalpha (b)-C-Fos-BirA-His×6 fusion protein (284 a.a) ("His×6" disclosed as SEQ ID NO: 18) was cloned into pMT/V5 fly cell expression vector between Nco I (854) to Xba I (1711). The fusion protein includes I-Aalpha (d) (195 a.a.), followed by C-Fos though a GS linker (6 a.a.), and then BirA sequence and 6×His (SEQ ID NO: 18).

As shown in FIG. 1, pMHC class II-NP therapy (pMOG$_{38-49}$/IA$^b$-coated NPs) reduces the severity of established EAE in C57BL/6 mice. B6 mice were immunized with pMOG$_{35-55}$ in CFA and treated with pertussis toxin i.v. Mice were scored for signs of EAE using established criteria over a 15-point scale. Affected mice were treated with two weekly doses of 7.5-22.5 μg of pMOG$_{38-49}$-coated NPs, beginning 21 days after immunization. Importantly, this effect is associated with systemic expansion of cognate autoreactive T-cells (FIG. 4). Furthermore, whereas the spinal cords of untreated mice had significant demyelination and dense mononuclear cell infiltrates of the white matter (FIG. 5), pMHC-NP-treated mice had significantly less demyelination and mononuclear cell infiltrates (FIG. 6). FIGS. 7 and 8 show representative examples for the spinal cord edges (2 mice each). Here, again, pMHC-NP-treated mice have significantly less demyelination as well as lower mononuclear cell infiltration. Thus, the pMHC-NP therapeutic approach induces clinically significant responses in different diseases (T1D, EAE), animal models and genetic backgrounds (NOD, C57BL/6).

These studies provide evidence of dose-dependent efficacy and feasibility of treatments for MS using MS-antigen-MHC-nanoparticle complexes.

Example 2. Process for Making Antigen-MHC-Nanoparticle Complexes

Inorganic nanoparticles (iron oxide=IONP; gold=GNPs) of a desired size. IONPs are produced via thermal decomposition. IONPs synthesized as such are biocompatible and can be PEGylated for protein conjugation. To coat pMHC and/or other proteins onto IONPs, surfactant-coated NPs are reacted with functionalized PEG linkers of the appropriate length. The linkers are purified by HPLC and characterized by $^1$H-NMR, MALDI/GPC and GPC, to confirm chemical identity, purity, molecular weight and polydispersity. Similar linkers and approaches can be used to coat GNPs, except that the linkers will have a thiol (SH) group at their NP-binding end.

Example 3. Size, Density, and Exposure of pMHC-Coated Nanoparticles

I. Synthesis and Characterization of Gold-Based pMHC-Coated NP

Figure 11:
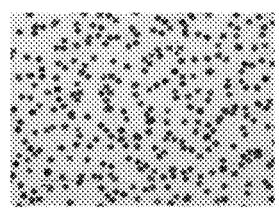
FIG. 11 shows representative TEM image of pMHC-coated gold NPs (~14 nm) concentrated at high densities (~5×10$^{13}$/ml) and monodispersed. Mag: 50,000×.

Gold nanoparticles (GNPs) of specific sizes were synthesized. The size, density, surface charge and monodispersity of the GNP preparations are measured using spectrophotometry, transmission electron microscopy (TEM) and dynamic light scattering. The GNP samples are then concentrated and conjugated with mono-specific pMHC complexes using different approaches as described below. Applicants have developed methods to quantitate the pMHC valency per GNP and to concentrate the pMHC-coated GNP preparations of different sizes at high densities (~10$^{14}$/ml) without compromising monodispersion (FIG. 11).

II. Characterization of the pMHC Binding Capacity of GNPs pMHC complexes were coated onto GNPs of various sizes using two different approaches: (i) random binding of pMHC to the GNP surface via electrostatic interactions; and (ii) directional binding through a thiol-PEG-NH$_2$ linker (in this case, an additional thiol-PEG linker as GNP stabilizer was used to prevent aggregation). It was believed that the first approach would enable very high ligand densities (of pMHC per GNP) while compromising the directionality of pMHC binding (i.e. only a fraction of the molecules might become available for recognition by cognate T-lymphocytes). The second approach aimed to generate pMHC-coated GNPs carrying lower densities of pMHC but bound directionally, via their C-termini. Both approaches were tested on GNPs of various diameters, ranging from 14 to 40 nm. It was confirmed that, for both approaches, the pMHC-binding capacity of GNPs is a function of size, and more specifically surface area (higher number of pMHCs on bigger NPs). Surprisingly, it was found that PEG mediated-binding not only ensures the directionality of binding but also enhances the binding capacity of individual GNPs (contrary to initial expectations). Table 1 below summarizes the data.

TABLE 1

| pMHC binding capacity of GNPs | | | |
| --- | --- | --- | --- |
| Diameter (nm) | Surface area: (×10$^2$ nm$^2$) | pMHCs/GNP (absorption) | pMHCs/GNP (linker) |
| 14 | 7 | | 212 |
| 20 | 12 | | 3,750 |
| 30 | 28 | 335 | |
| 40 | 50 | 2,850 | 5,250 |

III. Agonistic Activity Versus pMHC Content

Figure 12:
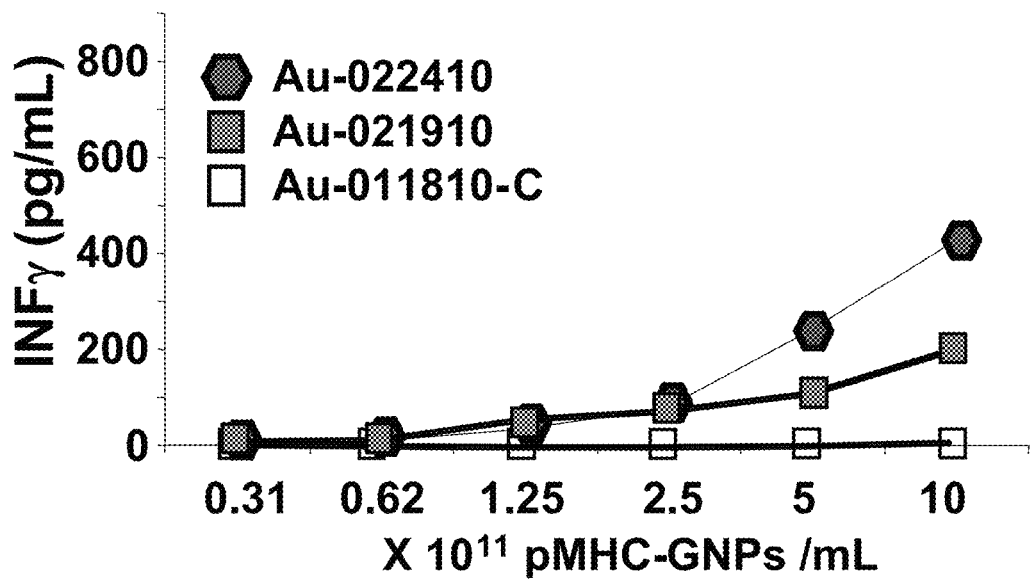
FIG. 12 shows the effects of pMHC (GNP) dose and pMHC valency on the agonistic properties of pMHC-coated NPs. The Figure compares the amounts of IFNγ secreted by cognate 8.3-CD8+ T-cells in response to two different pMHC-NP samples (both consisting of ~2×10$^{13}$ NPs of 14 nm in diameter/ml). Au-022410 and Au-21910 carried ~250 and ~120 pMHCs/NP, respectively. Au-011810-C carried ~120 control pMHCs/NP.

The effects of pMHC valency, GNP size, GNP density and coating strategy on the functional (agonistic) activity of pMHC-coated GNPs in vitro were tested. The ability of various IGRP$_{206-214}$-K$^d$-GNP preparations to activate cognate (IGRP$_{206-214}$-specific) naive CD8+ T cells (herein referred to as '8.3-CD8+ T-cells') derived from T-cell receptor (TCR) transgenic NOD mice (or 8.3-NOD mice) were compared. The first set of experiments aimed to compare the effects of IGRP$_{206-214}$-K$^d$ (pMHC) valency over a range of GNP densities in the culture. GNPs conjugated with a control (non-cognate) pMHC complex (Tum-K$^d$) were used as negative controls. As expected, IGRP$_{206-214}$-K$^d$-coated (but not TUM-K$^d$-coated) GNPs activated these T cells (as measured by IFNγ production), and they did so in a GNP dose-(hence pMHC dose)-dependent manner. FIG. 12 shows an experiment using ~14 nm GNPs coated with different numbers of pMHC molecules/GNP using the linker method. FIG. 12 compares the amounts of IFNγ secreted by cognate 8.3-CD8+ T-cells in response to two different pMHC-GNP samples (both consisting of ~2×10$^{13}$ GNPs of 14 nm in diameter/ml). Au-022410 and Au-21910 carried ~250 and ~120 pMHCs/GNP, respectively. Au-011810-C carried ~120 control pMHCs/GNP. GNPs coated with ~2-fold higher numbers of pMHC complexes/GNP had superior agonistic activity. Thus, the agonistic activity of pMHC-coated GNPs is a function of total pMHC (GNP) content. These results were counter-intuitive as the state of the art would suggest that, in the absence of costimulatory molecules on the NPs, increasing the numbers of pMHCs on individual NPs would also increase avidity and should promote deletion (cell death), rather than proliferation and cytokine secretion from cognate T-cells. This would be true for both low avidity and high avidity T-cells. For example, previous work by the Applicants (Han et al., (2005) Nature Medicine 11(6):645-652) and others indicated that peptides recognized with high avidity or peptides recognized with low avidity but given a high concentrations have an increased ability to delete cognate T cells in vivo. Therefore, in the context of therapeutic delivery of intravenous antigen-MHC-coated nanoparticles or soluble peptides, cognate T-cells should undergo deletion in a peptide affinity and dose-dependent manner. This expectation was not met by the data shown in FIG. 12.

IV. A Valency Threshold in the Agonistic Activity of Peptide-MHC-Nanoparticle Complexes To further investigate the role of peptide-MHC (pMHC) valency on the agonistic properties of pMHC-conjugated nanoparticles (pMHC-NPs), the ability of 8 nm diameter iron-oxide ($Fe_3O_4$) NPs covalently coupled with increasing numbers of $IGRP_{206-214}/K^d$ pMHC monomers, to trigger the secretion of IFN-gamma (IFNγ) by cognate ($IGRP_{206-214}/K^d$-specific) CD8+ T cells (herein referred to as 8.3-CD8+ T-cells) in vitro was compared. As shown in Table 2, 8.3-CD8+ T cells produced negligible amounts of IFNγ when cultured in the presence of NPs coated with 8 pMHC monomers per NP, but produced substantially higher amounts of IFNγ in response to NPs coated with higher pMHC valencies, even as low as 11 pMHC monomers/NP, in a dose-response manner.

TABLE 2

Secretion of IFNγ by 8.3-CD8+ T cells in response to NPs conjugated with increasing pMHC valencies (at $5 \times 10^{11}$ NPs/mL)

| Nanoparticles (NPs) | Core property | Core size (nm) | pMHC Valency | IFNγ responses (ng/mL) |
|---|---|---|---|---|
| IGRP-SFPM-110512 | Fe3O4 | 8 | 8 | 0.03 |
| IGRP-SFP-102912 | Fe3O4 | 8 | 11 | 0.4 |
| IGRP-SFP-012011 | Fe3O4 | 8 | 14 | 0.2 |
| IGRP-SFP-031511 | Fe3O4 | 8 | 15 | 0.15 |
| IGRP-SFP-051211 | Fe3O4 | 8 | 31 | 0.7 |
| IGRP-SFP-100711 | Fe3O4 | 8 | 39 | 0.9 |
| IGRP-SFP-011411 | Fe3O4 | 8 | 54 | 2.3 |

Figure 13:
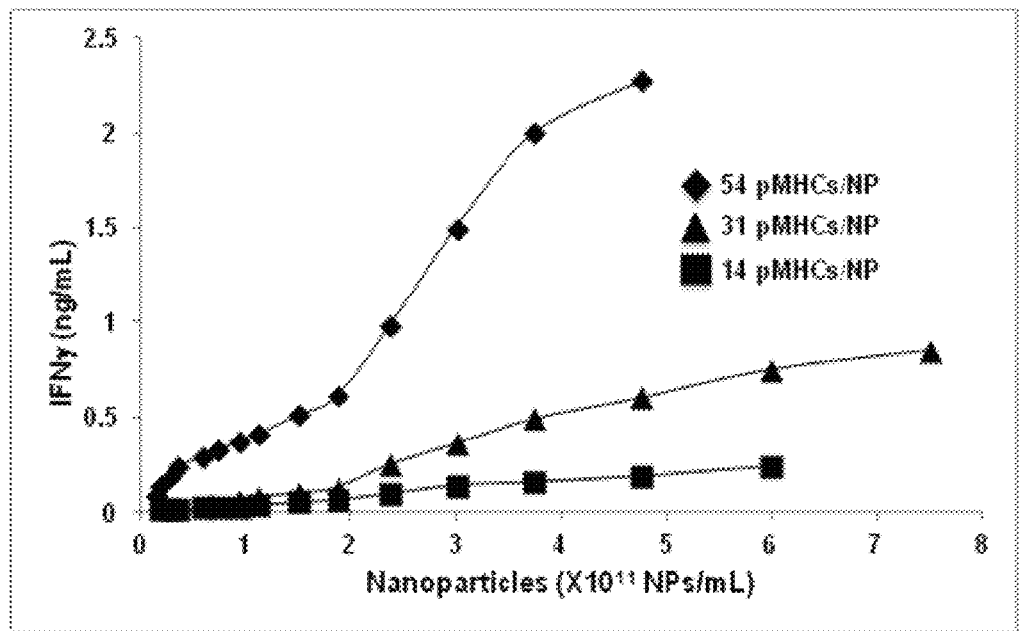
FIG. 13 demonstrates the pMHC-NP-induced secretion of IFNγ by 8.3-CD8+ T cells as a function of pMHC valency. 8.3-CD8+ T-cells (2.5×10$^5$ cells/ml) were cultured with increasing numbers of NPs coated with three different IGRP$_{206-214}$/K$^d$ valencies. IGRP$_{206-214}$ comprises the antigenic peptide VYLKTNVFL (SEQ ID NO: 19).
Figure 14:
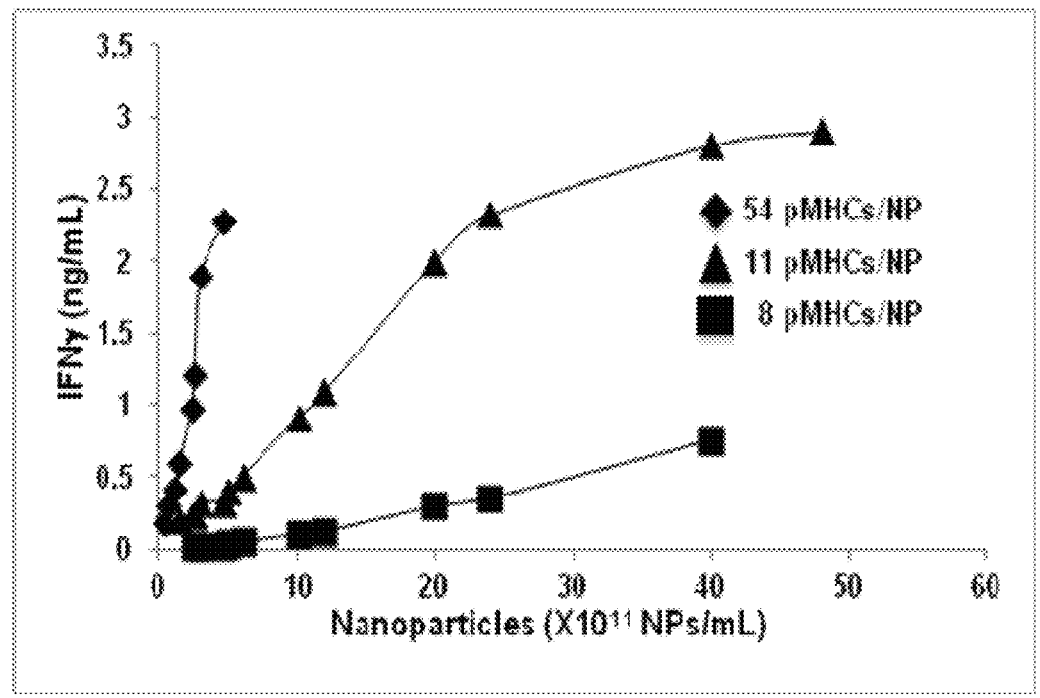
FIG. 14 shows that the lower agonistic activity of pMHC-NPs can be compensated by increasing the pMHC-NP density but only above a threshold of pMHC valency. Graph compares the agonistic activity of three different pMHC-NP preparations (carrying three different valencies of pMHC) over a range of NP densities. Note that NPs carrying 8 pMHCs, unlike those carrying 11 pMHCs, cannot adequately trigger IFNγ secretion even at high pMHC-NP densities, as compared to NPs carrying 11 and 54 pMHCs per NP.

This positive effect of pMHC valency on the agonistic activity of pMHC-NPs was maintained over a range of pMHC-NP densities (FIG. 13). Remarkably, however, whereas $25 \times 10^{11}$ NPs (per ml) carrying 11 pMHCs/NP had similar agonistic activity as $5 \times 10^{11}$ NPs (per ml) carrying 54 pMHCs/NP, increasing the number of NPs carrying 8 pMHCs/NP to values as high as $40 \times 10^{11}$ NPs/ml had minimal effects (FIG. 14). Taken together, these results indicate that there is a threshold of pMHC valency, lying between 9 and 11 pMHCs/NP, below which relatively large increases in the number of NPs (i.e., 5-fold) cannot overcome the low agonistic activity of pMHC-NPs coated at low valencies (it is noted that that the use of $>50 \times 10^{11}$ NPs in these in vitro experiments is not informative due to cellular toxicity caused by high NP densities).

Figure 15:
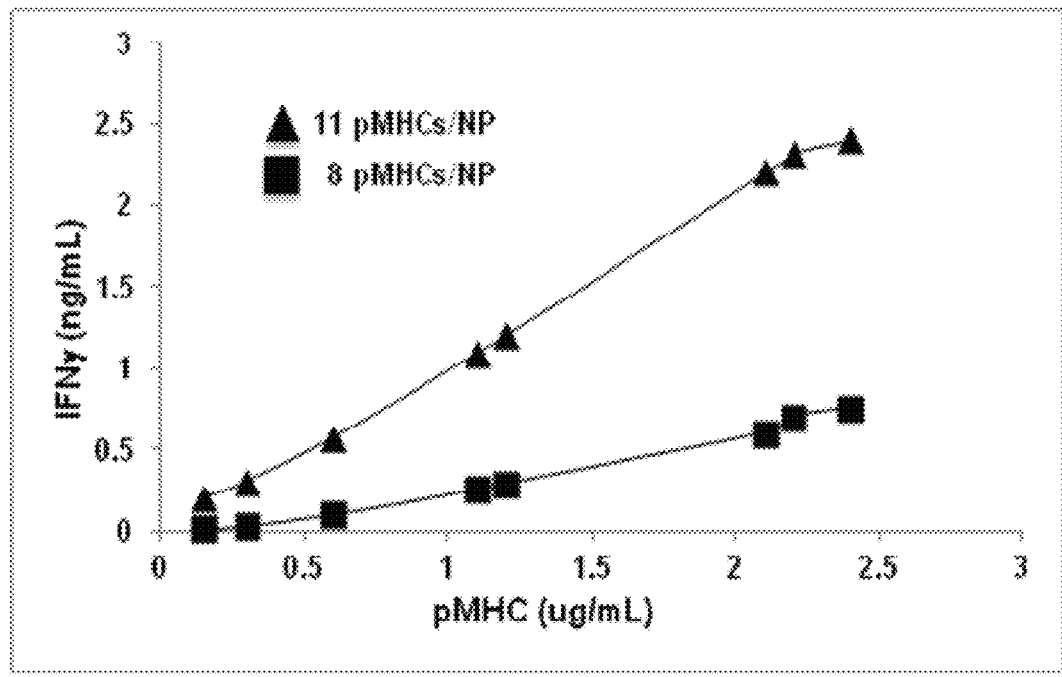
FIG. 15 shows the effects of pMHC valency threshold on the agonistic properties of pMHC-NPs as a function of total pMHC input.

This pMHC valency threshold effect is further illustrated in FIG. 15, where the IFNγ secretion data are normalized to the concentration of total pMHC delivered by the coated NPs in the cultures. NPs carrying 11 pMHCs/NP triggered significantly higher IFNγ responses over a range of pMHC concentrations than those triggered by NPs carrying 8 pMHCs/NP. Furthermore, differences in the agonistic properties of these two NP preparations increased substantially with total pMHC content. That is, differences in the agonistic properties of 2.4 µg/ml of pMHC delivered by the NPs as octamers versus monodecamers were much higher than differences in the agonistic properties of the same formulations at 10-fold lower concentrations of total pMHC.

Figure 16:
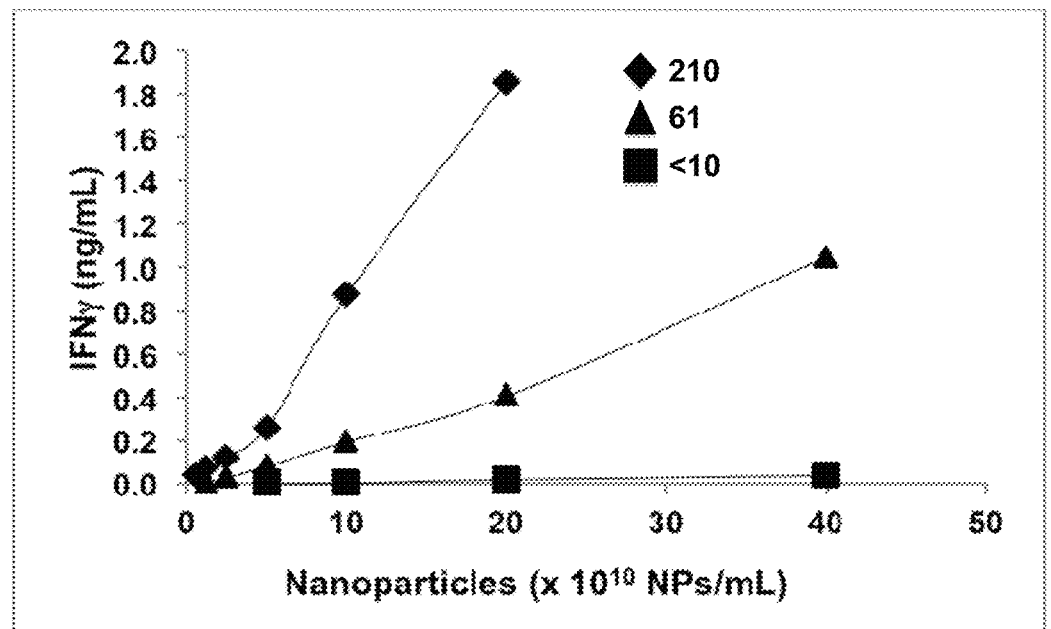
FIG. 16 shows the effects of pMHC valency on the agonistic activity of pMHC-NPs produced with larger iron oxide NP cores.

FIG. 16 shows that these profound effects of pMHC valency on the agonistic properties of pMHC-NPs can also be seen when using larger NPs (which can accept much higher pMHC valencies than the 8 nm NPs studied in FIGS. 13-15) used at lower NP densities (to normalize the total iron oxide content in the cultures). Whereas 18 nm diameter NPs carrying <10 pMHCs/NP had virtually no biological activity up to $4 \times 10^{11}$ NPs/ml, the agonistic activity of 18 nm diameter NPs carrying higher pMHC valencies increased linearly with NP density. Comparison of FIGS. 15 and 16 further shows that $2 \times 10^{11}$ 18 nm NPs delivering 61 pMHCs/NP have similar agonistic activity than $2 \times 10^{11}$ 8 nm NPs delivering a similar number (54) of pMHCs/NP, indicating that the effects of pMHC valency are not significantly affected by NP volume.

Taken together, these data demonstrate that pMHC-coated NPs acquire powerful agonistic activity above a certain pMHC valency threshold (lying between 9 and 11 pMHCs/NP). Increases in either pMHC valency or NP density can enhance the agonistic properties of pMHC-NPs carrying "threshold" or "supra-threshold" pMHC-valencies but not the agonistic properties of NPs carrying "infra-threshold" pMHC valencies.

V. Agonistic Activity Versus NP Size and Density

Figure 17:
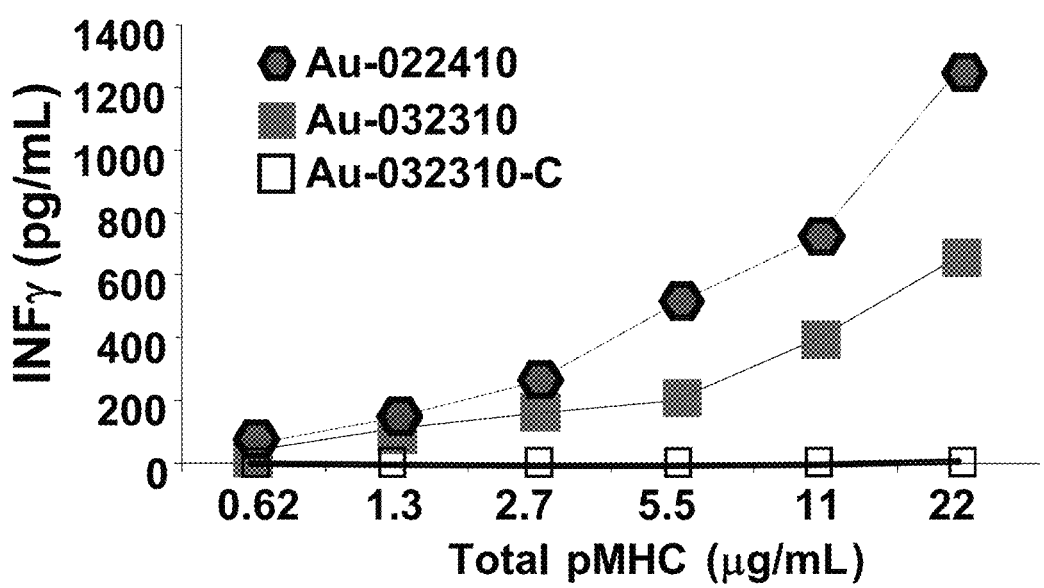
FIG. 17 shows the effect of size on agonistic activity. Au-0224-15 were 14 nm GNPs coated with a relatively low pMHC valency but prepared at a high density; Au-0323-40 were 40 nm GNPs coated with high pMHC valency but at low density. Au-0224-15 had superior agonistic activity than the Au-0323-40 sample.

Further analysis indicated that total pMHC content is not the only factor affecting the agonistic activity of pMHC-NPs in vitro and that NP size also plays an important independent role. This was investigated by comparing the agonistic activity of two pMHC-GNP samples of different size (14 and 40 nm in diameter, respectively) and different pMHC valencies but under conditions of similar total pMHC content. In the experiment shown in FIG. 17, 14 nm GNPs carrying ~200 pMHC molecules/GNP, and 40 nm GNPs carrying ~5,000 pMHCs/GNP were used. The GNP densities of these two samples was adjusted (to $3 \times 10^{13}$ and $10^{12}$ GNPs/mL, respectively) to adjust the total pMHC content in each sample to ~450 ug/ml. Notably, 8.3-CD8+ T cells responded significantly better to the 14 nm pMHC/GNP compound than to the 40 nm one over a range of total pMHC contents, despite the fact that the latter were decorated with significantly more pMHC complexes than the former. This suggested that GNP density (more GNPs/cognate T-cell) is key. In other words, $4 \times 40$ nm NPs carrying 1000 pMHCs/GNP (4000 pMHCs) would be less desirable than $40 \times 10$ nm NPs carrying 100 pMHCs/GNP (4000 pMHCs). Thus, when taken together these data suggest that optimal pMHC-GNP preparations are those comprised of small GNPs used at high pMHC densities. Increasing pMHC valency on these small NPs further increase their surprising and unexpected agonistic properties.

VI. Agonistic Activity Versus pMHC Exposure

Figure 18:
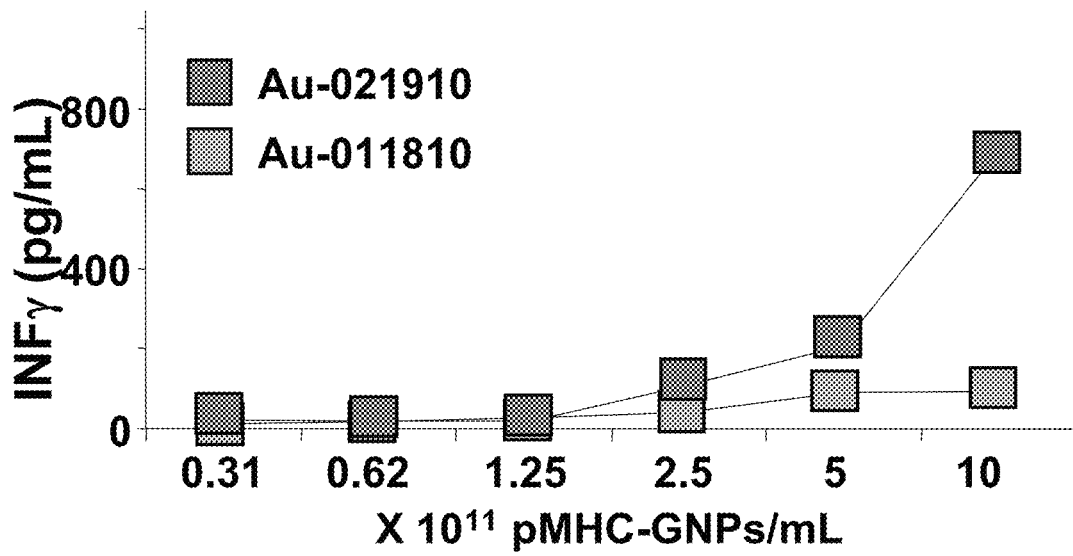
FIG. 18 shows the effect of protective PEGs on the function of pMHC-GNPs. Au-021910 consisted of ~2×10$^{13}$ GNPs of 14 nm in diameter/ml protected by 2 kD thiol-PEGs and coated with ~120 pMHCs/GNP. Au-012810 GNPs (also ~2×10$^{13}$ 14 nm GNPs/ml) were protected by 5 kD thiol-PEGs and were coated with ~175 pMHCs/GNP. Sample Au-021910 had superior agonistic activity.

As noted above, the pMHC-coated GNP samples are produced by co-coating GNPs with a 3.4 kD thiol-PEG-NH$_2$ linker (as acceptor of pMHC carboxitermini) with a thiol-PEG linker that functions as GNP stabilizer. To investigate if the length of the stabilizing thiol-PEG linker influences its GNP anti-aggregation properties, the ability of the thiol-PEG-NH$_2$ linker to bind pMHC molecules and/or the agonistic properties of pMHC-coated GNPs, pMHC-coated GNPs prepared using stabilizing linkers of different sizes (2 kD and 5 kD, shorter and longer than the pMHC-acceptor linker, respectively) were compared. It was found that both linkers had similar anti-aggregation properties, and that the 5 kD linker did not inhibit binding of pMHC to the shorter 3.4 kD thiol-PEG-NH$_2$ linker. Notably, however, pMHC-GNPs that were protected by the shorter (2 kD) thiol-PEG had superior agonistic activity in vitro than those co-coated with the longer (5 kD) thiol-PEG (FIG. 18). This suggests that long protective thiol-PEG linkers shield pMHC molecules bound to the acceptor linker from exposure to cognate T cells.

Figure 19:
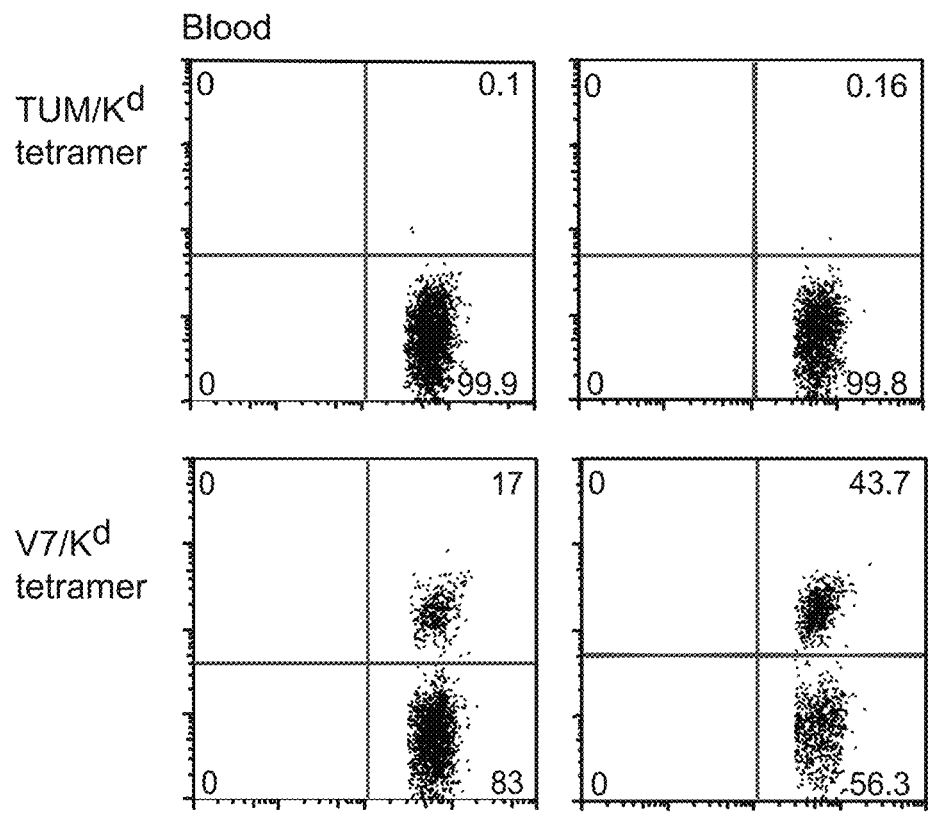
FIG. 19 shows the Efficient expansion of NRP-V7-reactive CD8+ T-cells by NRP-V7/Kd-coated gold NPs. 3×10$^{12}$ NPs (~10 nm in size) carrying 25 µg of pMHC (150 pMHC/NP) were used. Pre-diabetic 10 wk-old NOD mice were treated with two weekly injections of NRP-V7/kd-coated gold NPs for 5 weeks. TUM/Kd tetramer is a negative control. Each column of panels corresponds to a different mouse.

VII. Small NPs Covalently Coupled to High Densities of pMHC Afford Maximum Autoregulatory T-Cell Expansion Effects In Vivo Nanoparticles having an average diameter of about 10 nm and coupled to either NRP-V7/K$^d$ (also referred to as IGRP$_{206-214}$-K$^d$) or TUM/K$^d$ (control) were made in accordance with the methods described herein, and tested for their ability to induce expansion of cognate autoregulatory CD8+ T cells in vivo. FIG. 19 shows the results of an experiment in which antigen-MHC-GNPs were injected intravenously into 10 week-old wild-type NOD mice mice bi-weekly for 5 consecutive weeks. Changes in the size of the cognate T-cell population in the circulation and different lymphoid tissues in response to therapy were assessed by staining cell suspensions with fluorescently-labeled antigen-MHC tetramers (both cognate as well as irrelevant control tetramers). Administration of 10-100 fewer GNPs than what was has previously been shown in the art (See, for example, Tsai et al. (2010) Immunity 32(4):568-580) in which nanoparticles coated with 1-8 pMHCs were tested) but coated with 150 antigen-MHCs per GNP resulted in substantially higher expansions (FIG. 19). They expanded CD8+ T-cells in vivo to levels several fold higher (up to 44% of all circulating CD8+ T-cells) than those Applicants typically obtain with nanoparticles coated with a pMHC at a valency of about 8 (1-2% cells in blood; See, for example, Tsai et al., Immunity, 2010, FIG. 1C). The above data indicate that small nanoparticles coated with high antigen-MHC valencies afford maximum T-cell expansion effects. These results were unexpected. Accordingly, it is not the overall avidity of the pMHC-NP-T-cell interaction that is responsible for therapeutic effect, but rather the avidity of the precursor population that gives rise to the T-cells that expand in response to pMHC-NP therapy. This interpretation is consistent with the data described herein and implies that valency of pMHCs on NPs should increase the therapeutic efficacy of pMHC-NPs.

Figure 20:
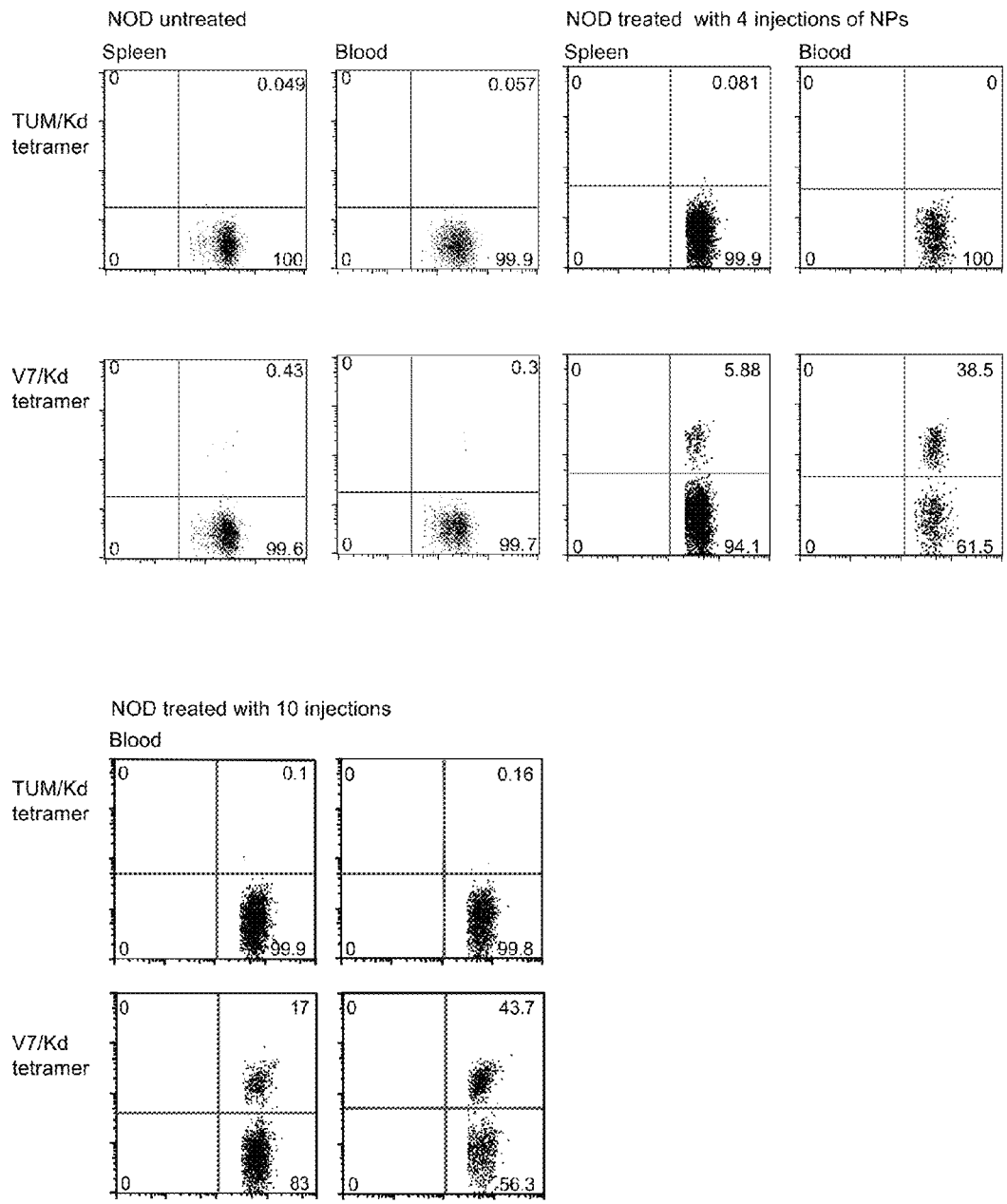
FIG. 20 depicts the large expansion of cognate CD8+ T-cells in mice treated with pMHC-coated NPs. 3×10$^{12}$ IGRP$_{206-214}$/K$^d$-NPs (~10 nm in size) carrying 25 µg of pMHC (150 pMHC/NP) were used. Upper panel: profile of a mouse sacrificed after 4 doses. Bottom panel: profile of two different mice after 10 injections (blood only).
Figure 21:
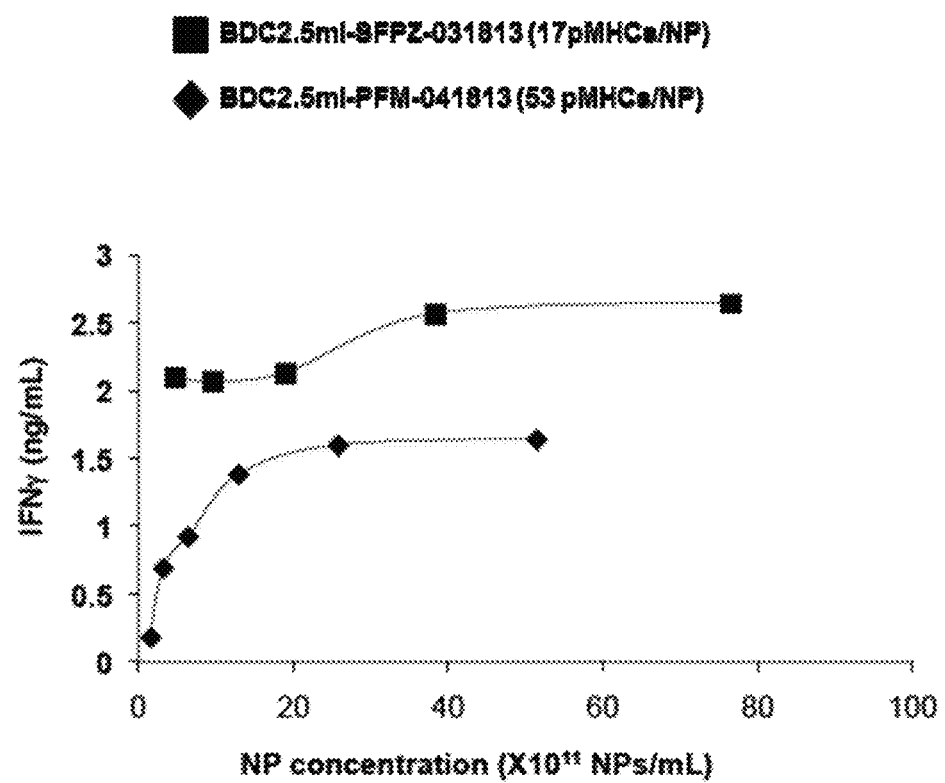
FIG. 21 demonstrates that the same principles for pMHC class I-Np complexes apply to pMHC class II-coated Nps (see FIG. 18). Note that pMHC class II pMHC-Nps (BDC2.5mi-coated 6-8 nm nanoparticle particles (SFPZ) coated with 17 pMHCs have higher agonistic activity than PFM (20-25 nm) particles coated with 53 pMHCs per NP. This confirms that with both class I-pMHC Nps and class II-pMHC-Nps it is not the absolute valency of pMHC but rather the pMHC density that matters. As demonstrated by the increased pMHC-NP-induced secretion of IFNγ by CD4+ T cells as a function of pMHC density.

Example 4. Large Expansion of Cognate CD8+ T-Cells by pMHC-GNPs Coated at Higher pMHC Valencies It was next determined whether pMHC-NPs have the potential to induce massive expansions of cognate T-cells in vivo. This was done by treating mice with several injections of 3×10$^{12}$ 10-14 nm NPs carrying 25 ug of total pMHC (~150 IGRP$_{206-214}$/Kd molecules per NP). As shown in FIG. 20, mice treated with 10 doses (twice a week for 10 week) displayed massive expansions of cognate IGRP$_{206-214}$ (NRP-V7)-reactive CD8+ T-cells in peripheral blood as compared to their untreated counterparts (from <0.4 to >17 or 47% CD8+ T-cells) (lower panels). Such expansion was already seen in a mouse that was sacrificed after 4 doses of pMHC-NPs (upper panels). The pMHC-NP-expanded cells specifically bound cognate but not non-cognate pMHC tetramers (NRP-V7/K$^d$ vs. TUM/K$^d$, respectively).

Example 5. Preparation of pMHC Conjugated Gold NanoParticles pMHC Conjugated Gold NanoParticle Preparation (pMHC-GNPs, 12 and 30 nm). Preparation of GNPs.

GNPs were prepared by heating D.D. water (200 mL) in a ball flask in a silicon oil bath till boiling. A solution of 1% HAuCL$_4$ (4 mL) was then added into boiling water. The solution was stirred for 10 min before adding of 1% Na Citrate solution. For 12 nm GNPs, 12 mL Na Citrate solution was added. For 30 nm GNPs, 12 mL Na Citrate solution was added. A wine color appears immediately after adding Na Citrate solution. To complete the reaction, GNP solution was stirred for 30 minutes more. This is a modification of the method described in Levy, R. et al. ("Rational and combinatorial design of peptide capping ligands for gold nanoparticles." J Am Chem Soc 126, 10076-84 (2004)) which is herein incorporated by reference.

Surface Modification of GNPs.

GNPs were pegylated by addition of 25 mM thiol-PEG-NH$_2$ (M.W. 3,400) and 50 mM thiol-PEG (M. W. 2,000, PEG/GNP ratio 10,000:1) into GNP solution. The solution was stirred for 5 hours at room temperature. Pegylated GNPs were then washed with 3×30 mL sterilized D. D. water to remove excess PEGs, and resuspended in 40 mL of 100 mM MES (C$_6$H$_{13}$NO$_4$S.xH$_2$O) buffer, pH 5.5.

pMHC Conjugation.

pMHCs (IGRP$_{206-214}$/Kd, 4 mg) was added into solution of pegylated GNPs, drop-by-drop with mild stirring at room temperature. The mixture is stirred for one hour before the addition of 20 mg 1-Ethyl-3-(3-dimethylaminopropyl) carbodiimide (EDC). The mixture is stirred for additional 4 hrs. pMHC-GNPs conjugates are then washed with 40 mL Phosphate Buffered Saline (PBS, PH 7.2-7.4) for three times, and resuspended in 8 mL PBS.

Example 6. Preparation of pMHC Conjugated Gold NanoParticles

Preparation of pMHC Conjugated GNPs (pMHC-GNPs, 2-10 nm). Prepare GNPs (2-5 nm).

GNPs of 2-5 nm were prepared by dissolving 250 mg (for 2 nm GNPs) or 50 mg (for 4 nm GNPs) Dodecylamine in 10 mL of DDAB solution (100 mM Didodecyldimethylammonium bromide (DDAB) in Toluene). Secondly, 100 mg Tetrabutylammonium borohydride (TBAB) was dissolved in 4 mL of DDAB solution. Solutions of Dodecylamine and TBAB were then mixed in a 50 mL three-neck flask, stirring under nitrogen. 34 mg AuCl$_3$ was resolved in 4.5 mL DDAB solution, and injected quickly into a mixture of TBAB and Dodecylamine solution. Solution becomes deep red immediately, indicating the formation of GNPs. The mixture was continuously stirred for 30 min, and 15 mLs of ethanol were added into the mixture. The mixture was then spun at 4,100×g for 12 min to precipitate GNPs.

Prepare GNPs (6-10 nm).

To prepare GNPs of 6-10 nm Decanoic acid (172 mg) was first dissolved in 10 mL Toluene, and then mixed with various amounts of TBAB solution (4 and 1 mL for 6 and 10 nm GNPs, respectively) in a 50 mL three-neck flask, when stirring under nitrogen. $AuCl_3$ (34 mg dissolved in in 4.5 mL DDAB stock solution) was then quickly injected into the mixture of TBAB and Decanoic acid solution. The solution became deep red immediately. The mixture was continuously stirred for 30 min, and 15 mL ethanol was added into the mixture. The mixture is then spun at 4,100×g for 12 min to precipitate GNPs.

Surface Modification of GNPs.

GNPs were resuspended in 20 mL of 0.1 M mercaptopropanoic acid (MPA) in methanol, pH 10 and stirred for one hour at room temperature. 10 mL ethyl acetate was then added. The mixture was then spun at 4,100×g for 15 min. The precipitated GNPs were then washed with 30 mL sterilized D.D. water for three times, and resuspended in 20 mL 100 mM MES ($C_6H_{13}NO_4S.xH_2O$) buffer, pH 5.5. To this mixture, solutions of 0.5 M Polyoxyethylene bis(amine) (at 10,000:1 PEG/GNP ratio) and 0.1M 1-Ethyl-3-(3-dimethylaminopropyl) carbodiimide (EDC) (final EDC concentration 2 mM) were added. The mixture was then stirred for 4 hours. The pegylated GNPs were washed with 3×30 mL sterilized D.D. water to remove excess PEG and EDC.

pMHC Conjugation.

Pegylated GNPs were resuspended in 20 mL 100 mM MES ($C_6H_{13}NO_4S.xH_2O$) buffer, pH 5.5. pMHCs (5 mg/mL, total 10-30 mg) were then added to resuspended GNPs (500:1 pMHC/GNP ratio), drop-by-drop, and stirred for 1 hour at room temperature before adding 0.1M 1-Ethyl-3-(3-dimethylaminopropyl) carbodiimide (EDC) (final EDC concentration 2 mM). The mixture was stirred for 4 more hours. pMHC-GNPs conjugates were washed three with 40 mL Phosphate Buffered Saline (PBS, PH 7.2-7.4), and then resuspended in 10-20 mL PBS.

pMHC Optimization.

The optimal pMHC-NP design consists of small particles coated with pMHC monomers at the highest possible density, which yields pMHC complexes separated by 3-4 nm. pMHC-NPs designed following these principles have optimal potency (maximal agonistic activity and Treg expanding properties at lower doses of total pMHC). This has been confirmed experimentally for the findings for class I pMHC-Nps is also true for pMHC class II-coated Np. When used at optimal density and dose of pMHC, both pMHC class I and class II-coated NPs, can expand cognate autoregulatory T-cells. Thus, the ideal pMHC-NP design involves the ability to deliver densely packed pMHCs on NPs.

This is supported by two experimental observations: (1) larger NPs coated with similar number of pMHCs than their smaller counterparts, particularly at threshold valency values (i.e. 10 pMHCs/NP) were significantly less agonistic, independently of total pMHC input, the threshold value spacing individual pMHCs at 10 nm requires 60 pMHCs/NP and >120 pMHCs to reach the 3-4 nm spacing distance; and (2) small NPs coated at very high densities of pMHC has the highest agonisitic activity, also independently of total pMHC input. Thus, reductions in the pMHC distance (i.e. from the 10 nm threshold distance to 2-4 nm) by increasing pMHC density increases the overall avidity and TCR signaling capacity of the pMHC-NP-T-cell interaction. Thus, the threshold for agonistic activity is defined by pMHC molecular density (pMHC intermolecular distance) on the NP surface rather than by pMHC molecular number.

Collectively, this lays the groundwork for the optimal design of pMHC-NP formulations aimed at expanding autoantigen-specific regulatory T-cells in vivo for the treatment of autoimmune disorders. Applicant has shown that optimal formulations can yield massive expansions of autoantigen-specific regulatory T-cells in vivo to frequencies as high as 1 in 2 circulating CD8+ or CD4+ T-cells at extremely low doses of pMHC-NPs. Since therapeutic levels are significantly lower than those inducing these massive expansions, this approach benefits from a large safety and efficacy margin that should enable the treatment of aggressive autoimmune conditions.

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

SEQUENCE LISTING

```
SEQ ID NO: 1:
pMOG₃₈₋₄₉ antigen: • GWYRSPFSRVVH.
```

SEQ ID NO: 2: Protein sequence of vector comprising $pMOG_{38-49}$ antigen (FIGS. 9A-9B).

SEQ ID NO: 3: DNA sequence of vector comprising $pMOG_{38-49}$ antigen (FIGS. 9A-9B).

What is claimed is:

1. A nanoparticle complex comprising: a nanoparticle core and multiple sclerosis-related antigen-MHC (pMHC) complexes operatively coupled to the nanoparticle core, wherein the nanoparticle core has a diameter from about 1 nm to about 100 nm and wherein the pMHC density on the nanoparticle core comprises from about 0.005 pMHC/100 nm$^2$ to about 25 pMHC/100 nm$^2$.

2. A kit comprising the complex of claim 1, and instructions for use.

3. The nanoparticle complex of claim 1, wherein the nanoparticle core has a diameter from about 1 nm to about 50 nm.

4. The nanoparticle complex of claim 1, wherein the nanoparticle core has a diameter from about 1 nm to about 20 nm.

5. The nanoparticle complex of claim 1, wherein the nanoparticle core has a diameter from about 5 nm to about 20 nm.

6. The nanoparticle complex of claim 1, wherein the nanoparticle core has a biodegradable layer on the outer surface of the nanoparticle core and the pMHC complexes are operatively coupled to the nanoparticle core or the biodegradable layer on the nanoparticle core.

7. The nanoparticle complex of claim 6, wherein the biodegradable layer comprises one or more of dextran, mannitol, or poly(ethylene glycol).

8. The nanoparticle complex of claim 6, wherein the nanoparticle core has a diameter from about 1 nm to about 50 nm.

9. The nanoparticle complex of claim 6, wherein the nanoparticle core has a diameter from about 1 nm to about 20 nm.

10. The nanoparticle complex of claim 6, wherein the nanoparticle core has a diameter from about 5 nm to about 20 nm.

11. The nanoparticle complex of claim 1 or 6, wherein the multiple sclerosis-related antigen of the pMHC complexes is an antigen derived from a protein selected from the group of myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, and 2'3'-cyclic nucleotide 3'-phosphodiesterase and myelin oligodendrocyte glycoprotein (MOG) or an antigen corresponding to a peptide having at least 80% identity to a peptide comprising the sequence of SEQ ID NO: 1 or 4-17, or an equivalent of each thereof.

12. The nanoparticle complex of claim 1 or 6, wherein the nanoparticle core is non-liposomal.

13. The nanoparticle complex of claim 1 or 6, wherein the pMHC complexes are covalently or non-covalently linked to the nanoparticle core or the biodegradable layer.

14. The nanoparticle complex of claim 1 or 6, wherein the pMHC complexes are covalently linked to the nanoparticle core or the biodegradable layer through a linker less than 5 kD in size.

15. The nanoparticle complex of claim 14, wherein the linker comprises polyethylene glycol.

16. The nanoparticle complex of claim 1 or 6, wherein the nanoparticle core is bioabsorbable and/or biodegradable.

17. The nanoparticle complex of claim 1 or 6, wherein the MHC of the pMHC complexes is a MHC class I or II protein.

18. The nanoparticle complex of claim 17, wherein the MEW class I protein comprises all or part of a HLA-A, HLA-B, HLA-C, HLA-E, HLA-F, HLA-G or CD-1 protein.

19. The nanoparticle complex of claim 17, wherein the MHC class II protein comprises all or part of a HLA-DR, HLA-DQ, or HLA-DP protein.

20. The nanoparticle complex of claim 1 or 6, wherein the ratio of the number of pMHC complexes to the nanoparticle core is from about 10:1 to about 500:1.

21. A composition comprising a therapeutically effective amount of the nanoparticle complex of claim 1 or 6, and a carrier.

22. A method for making, preparing or obtaining the nanoparticle complex of any one of claim 1-6 or 3-10, comprising coating or complexing the pMHC complexes onto the nanoparticle core or the biodegradable layer.

23. A method for expanding and/or developing populations of anti-pathogenic autoreactive T-cells in a subject with multiple sclerosis or a multiple sclerosis-related disorder, comprising administering to the subject an effective amount of the nanoparticle complex of any one of claim 1-6 or 3-10, thereby expanding and/or developing the populations of anti-pathogenic autoreactive T-cells.

24. The method of claim 23, wherein the multiple sclerosis-related disorder is selected from the group consisting of neuromyelitis optica (NMO) and neuropathic pain.

* * * * *